US012670978B2

(12) United States Patent
Mason et al.

(10) Patent No.: US 12,670,978 B2
(45) Date of Patent: *Jun. 30, 2026

(54) SYSTEM AND METHOD FOR USING AN ARTIFICIAL INTELLIGENCE ENGINE TO OPTIMIZE A TREATMENT PLAN

(71) Applicant: ROM TECHNOLOGIES, INC., Brookfield, CT (US)

(72) Inventors: Steven Mason, Las Vegas, NV (US); John Ashley, San Francisco, CA (US)

(73) Assignee: ROM Technologies, Inc., Brookfield, CT (US)

( * ) Notice: Subject to any disclaimer, the term of this patent is extended or adjusted under 35 U.S.C. 154(b) by 598 days.

This patent is subject to a terminal disclaimer.

(21) Appl. No.: 17/823,369

(22) Filed: Aug. 30, 2022

(65) Prior Publication Data

US 2023/0072368 A1 Mar. 9, 2023

Related U.S. Application Data

(63) Continuation-in-part of application No. 17/736,891, filed on May 4, 2022, now Pat. No. 12,347,543,
(Continued)

(51) Int. Cl.
G16H 20/30 (2018.01)
A63B 24/00 (2006.01)
G16H 50/30 (2018.01)

(52) U.S. Cl.
CPC ......... *G16H 20/30* (2018.01); *A63B 24/0062* (2013.01); *G16H 50/30* (2018.01); *A63B 2024/0065* (2013.01)

(58) Field of Classification Search
CPC ........ G16H 20/30; G16H 50/30; G16H 15/00; G16H 40/63; G16H 40/67; G16H 50/20;
(Continued)

(56) References Cited

U.S. PATENT DOCUMENTS 823,712 A 6/1906 Uhlmann
4,499,900 A 2/1985 Petrofsky et al.
(Continued)

FOREIGN PATENT DOCUMENTS

CA 3193419 A1 3/2022
CN 2885238 Y 4/2007
(Continued)

OTHER PUBLICATIONS

He, Jianxing et al. The practical implementation of artificial intelligence technologies in medicine. Nature Medicine; New York vol. 25, Iss. 1. Jan. 2019. (Year: 2019).*
(Continued)

*Primary Examiner* — Fawaad Haider

(74) *Attorney, Agent, or Firm* — Dickinson Wright PLLC; Jonathan H. Harder; Stephen A. Mason

(57) ABSTRACT

A method for updating a treatment plan. The treatment plan is associated with a user using a treatment apparatus to perform the treatment plan. The method includes receiving first data associated with a first diagnosis of the user. The method includes generating, based on the first data, an initial treatment plan to be performed on the treatment apparatus by the user. The method includes receiving second data associated with a first attribute of the user. The method includes generating, via an artificial intelligence engine, a machine learning model trained to generate an updated treatment plan based on the initial treatment plan and the second data.

16 Claims, 13 Drawing Sheets

Related U.S. Application Data which is a continuation-in-part of application No. 17/379,542, filed on Jul. 19, 2021, now Pat. No. 11,328,807, which is a continuation of application No. 17/146,705, filed on Jan. 12, 2021, now Pat. No. 12,191,018, which is a continuation-in-part of application No. 17/021,895, filed on Sep. 15, 2020, now Pat. No. 11,071,597.

(60) Provisional application No. 63/238,957, filed on Aug. 31, 2021, provisional application No. 63/113,484, filed on Nov. 13, 2020, provisional application No. 62/910,232, filed on Oct. 3, 2019.

(58) Field of Classification Search
CPC .... G16H 50/70; G16H 80/00; A63B 24/0062; A63B 2024/0065; A63B 2024/0093; A63B 21/00178; A63B 21/00181; A63B 21/0058; A63B 22/0605; A63B 24/0075; A63B 24/0087; A63B 2022/0652; A63B 2071/063; A63B 2071/0652; A63B 2071/0655; A63B 2071/0663; A63B 2071/068; A63B 2071/0683; A63B 2220/13; A63B 2220/16; A63B 2220/30; A63B 2220/51; A63B 2220/52; A63B 2225/20; A63B 2225/50; A63B 2230/06; A63B 2230/202; A63B 2230/207; A63B 2230/30; A63B 2230/42; A63B 2230/50; A63B 2022/0623; A61H 2230/06; A61H 2230/207; A61H 2230/30; A61H 2230/202; A61H 2230/42; A61H 2201/1215; A61H 2201/1261; A61H 2201/1633; A61H 2201/164; A61H 2201/1642; A61H 2201/1671; A61H 2201/501; A61H 2201/5012; A61H 2201/5043; A61H 2201/5046; A61H 2201/5048; A61H 2201/5061; A61H 2201/5064; A61H 2201/5069; A61H 2201/5071; A61H 2201/5092; A61H 2201/5097; A61H 2203/0431; A61H 2205/10; A61H 1/024; A61H 1/0214
USPC .......................................................... 705/24
See application file for complete search history.

(56) References Cited

U.S. PATENT DOCUMENTS

| | | | |
|---|---|---|---|
| 4,822,032 A | 4/1989 | Whitmore et al. |
| 4,860,763 A | 8/1989 | Schminke |
| 4,869,497 A | 9/1989 | Stewart et al. |
| 4,932,650 A | 6/1990 | Bingham et al. |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,356,356 A | 10/1994 | Hildebrandt |
| 5,361,649 A | 11/1994 | Slocum, Jr. |
| D359,777 S | 6/1995 | Hildebrandt |
| 5,429,140 A | 7/1995 | Burdea et al. |
| 5,458,022 A | 10/1995 | Mattfeld et al. |

| | | | |
|---|---|---|---|
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,007,459 A | 12/1999 | Burgess |
| D421,075 S | 2/2000 | Hildebrandt |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| 6,640,662 B1 | 11/2003 | Baxter |
| 6,652,425 B1 | 11/2003 | Martin et al. |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| 7,507,188 B2 | 3/2009 | Nurre |
| 7,594,879 B2 | 9/2009 | Johnson |
| 7,628,730 B1 | 12/2009 | Watterson et al. |
| D610,635 S | 2/2010 | Hildebrandt |
| 7,778,851 B2 | 8/2010 | Schoenberg et al. |
| 7,809,601 B2 | 10/2010 | Shaya et al. |
| 7,815,551 B2 | 10/2010 | Merli |
| 7,833,135 B2 | 11/2010 | Radow et al. |
| 7,837,472 B1 | 11/2010 | Elsmore et al. |
| 7,890,342 B1 | 2/2011 | Yruko |
| 7,955,219 B2 | 6/2011 | Birrell et al. |
| 7,969,315 B1 | 6/2011 | Ross et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,079,937 B2 | 12/2011 | Bedell |
| 8,113,991 B2 | 2/2012 | Kutliroff |

(56) References Cited

U.S. PATENT DOCUMENTS

| | | | |
|---|---|---|---|
| 8,172,724 | B2 | 5/2012 | Solomon |
| 8,177,732 | B2 | 5/2012 | Einav et al. |
| 8,287,434 | B2 | 10/2012 | Zavadsky et al. |
| 8,298,123 | B2 | 10/2012 | Hickman |
| 8,371,990 | B2 | 2/2013 | Shea |
| 8,419,593 | B2 | 4/2013 | Ainsworth et al. |
| 8,465,398 | B2 | 6/2013 | Lee et al. |
| 8,503,086 | B2 | 8/2013 | French |
| 8,506,458 | B2 | 8/2013 | Dugan |
| 8,515,777 | B1 | 8/2013 | Rajasenan |
| 8,540,515 | B2 | 9/2013 | Williams et al. |
| 8,540,516 | B2 | 9/2013 | Williams et al. |
| 8,556,778 | B1 | 10/2013 | Dugan |
| 8,607,465 | B1 | 12/2013 | Edwards |
| 8,613,689 | B2 | 12/2013 | Dyer et al. |
| 8,615,529 | B2 | 12/2013 | Reiner |
| 8,672,812 | B2 | 3/2014 | Dugan |
| 8,751,264 | B2 | 6/2014 | Beraja et al. |
| 8,784,273 | B2 | 7/2014 | Dugan |
| 8,818,496 | B2 | 8/2014 | Dziubinski et al. |
| 8,823,448 | B1 | 9/2014 | Shen |
| 8,845,493 | B2 | 9/2014 | Watterson et al. |
| 8,849,681 | B2 | 9/2014 | Hargrove et al. |
| 8,864,628 | B2 | 10/2014 | Boyette et al. |
| 8,893,287 | B2 | 11/2014 | Gjonej et al. |
| 8,911,327 | B1 | 12/2014 | Boyette |
| 8,979,711 | B2 | 3/2015 | Dugan |
| 9,004,598 | B2 | 4/2015 | Weber |
| 9,044,630 | B1 | 6/2015 | Lampert et al. |
| 9,167,281 | B2 | 10/2015 | Petrov et al. |
| D744,050 | S | 11/2015 | Colburn |
| 9,248,071 | B1 | 2/2016 | Brenda |
| 9,256,711 | B2 | 2/2016 | Horseman |
| 9,272,091 | B2 | 3/2016 | Skelton |
| 9,272,185 | B2 | 3/2016 | Dugan |
| 9,283,434 | B1 | 3/2016 | Wu |
| 9,295,878 | B2 | 3/2016 | Corbalis et al. |
| 9,311,789 | B1 | 4/2016 | Gwin |
| 9,312,907 | B2 | 4/2016 | Auchinleck et al. |
| 9,367,668 | B2 | 6/2016 | Flynt et al. |
| 9,409,054 | B2 | 8/2016 | Dugan |
| 9,443,205 | B2 | 9/2016 | Wall |
| 9,474,935 | B2 | 10/2016 | Abbondanza et al. |
| 9,480,873 | B2 | 11/2016 | Chuang |
| 9,481,428 | B2 | 11/2016 | Gros |
| 9,514,277 | B2 | 12/2016 | Hassing et al. |
| 9,566,472 | B2 | 2/2017 | Dugan |
| 9,579,056 | B2 | 2/2017 | Rosenbek et al. |
| 9,629,558 | B2 | 4/2017 | Yuen et al. |
| 9,640,057 | B1 | 5/2017 | Ross |
| 9,707,147 | B2 | 7/2017 | Levital et al. |
| 9,713,744 | B2 | 7/2017 | Suzuki |
| D794,142 | S | 8/2017 | Zhou |
| 9,717,947 | B2 | 8/2017 | Lin |
| 9,737,761 | B1 | 8/2017 | Govindarajan |
| 9,757,612 | B2 | 9/2017 | Weber |
| 9,773,330 | B1 | 9/2017 | Douglas |
| 9,782,621 | B2 | 10/2017 | Chiang et al. |
| 9,802,076 | B2 | 10/2017 | Murray et al. |
| 9,802,081 | B2 | 10/2017 | Ridgel et al. |
| 9,813,239 | B2 | 11/2017 | Chee et al. |
| 9,827,445 | B2 | 11/2017 | Marcos et al. |
| 9,849,337 | B2 | 12/2017 | Roman et al. |
| 9,868,028 | B2 | 1/2018 | Shin |
| 9,872,087 | B2 | 1/2018 | DelloStritto et al. |
| 9,872,637 | B2 | 1/2018 | Kording et al. |
| 9,914,053 | B2 | 3/2018 | Dugan |
| 9,919,198 | B2 | 3/2018 | Romeo et al. |
| 9,937,382 | B2 | 4/2018 | Dugan |
| 9,939,784 | B1 | 4/2018 | Berardinelli |
| 9,974,478 | B1 | 5/2018 | Brokaw |
| 9,977,587 | B2 | 5/2018 | Mountain |
| 9,993,181 | B2 | 6/2018 | Ross |
| 9,997,082 | B2 | 6/2018 | Kaleal |
| 10,004,946 | B2 | 6/2018 | Ross |
| 10,026,052 | B2 | 7/2018 | Brown et al. |
| D826,349 | S | 8/2018 | Oblamski |
| 10,055,550 | B2 | 8/2018 | Goetz |
| 10,058,473 | B2 | 8/2018 | Oshima et al. |
| 10,074,148 | B2 | 9/2018 | Cashman et al. |
| 10,089,443 | B2 | 10/2018 | Miller et al. |
| 10,111,643 | B2 | 10/2018 | Shulhauser et al. |
| 10,130,311 | B1 | 11/2018 | De Sapio et al. |
| 10,137,328 | B2 | 11/2018 | Baudhuin |
| 10,143,395 | B2 | 12/2018 | Chakravarthy et al. |
| 10,155,134 | B2 | 12/2018 | Dugan |
| 10,159,872 | B2 | 12/2018 | Sasaki et al. |
| 10,173,094 | B2 | 1/2019 | Gomberg et al. |
| 10,173,095 | B2 | 1/2019 | Gomberg et al. |
| 10,173,096 | B2 | 1/2019 | Gomberg et al. |
| 10,173,097 | B2 | 1/2019 | Gomberg et al. |
| 10,198,928 | B1 | 2/2019 | Ross et al. |
| 10,226,663 | B2 | 3/2019 | Gomberg et al. |
| 10,231,664 | B2 | 3/2019 | Ganesh |
| 10,244,990 | B2 | 4/2019 | Hu et al. |
| 10,258,823 | B2 | 4/2019 | Cole |
| 10,322,315 | B2 | 6/2019 | Foley et al. |
| 10,325,070 | B2 | 6/2019 | Beale et al. |
| 10,327,697 | B1 | 6/2019 | Stein et al. |
| 10,362,940 | B2 | 7/2019 | Tran |
| 10,369,021 | B2 | 8/2019 | Zoss et al. |
| 10,380,866 | B1 | 8/2019 | Ross et al. |
| 10,413,222 | B1 | 9/2019 | Kayyall |
| 10,413,238 | B1 | 9/2019 | Cooper |
| 10,424,033 | B2 | 9/2019 | Romeo |
| 10,430,552 | B2 | 10/2019 | Mihai |
| D866,957 | S | 11/2019 | Ross et al. |
| 10,468,131 | B2 | 11/2019 | Macoviak et al. |
| 10,475,323 | B1 | 11/2019 | Ross |
| 10,475,537 | B2 | 11/2019 | Purdie et al. |
| 10,492,977 | B2 | 12/2019 | Kapure et al. |
| 10,507,358 | B2 | 12/2019 | Kinnunen et al. |
| 10,542,914 | B2 | 1/2020 | Forth et al. |
| 10,546,467 | B1 | 1/2020 | Luciano, Jr. et al. |
| 10,569,122 | B2 | 2/2020 | Johnson |
| 10,572,626 | B2 | 2/2020 | Balram |
| 10,576,331 | B2 | 3/2020 | Kuo |
| 10,581,896 | B2 | 3/2020 | Nachenberg |
| 10,625,114 | B2 | 4/2020 | Ercanbrack |
| 10,646,746 | B1 | 5/2020 | Gomberg et al. |
| 10,660,534 | B2 | 5/2020 | Lee et al. |
| 10,678,890 | B2 | 6/2020 | Bitran et al. |
| 10,685,092 | B2 | 6/2020 | Paparella et al. |
| 10,741,285 | B2 | 8/2020 | Moturu |
| 10,777,200 | B2 | 9/2020 | Will et al. |
| D899,605 | S | 10/2020 | Ross et al. |
| 10,792,495 | B2 | 10/2020 | Izvorski et al. |
| 10,814,170 | B2 | 10/2020 | Wang et al. |
| 10,857,426 | B1 | 12/2020 | Neumann |
| 10,867,695 | B2 | 12/2020 | Neagle |
| 10,874,905 | B2 | 12/2020 | Belson et al. |
| D907,143 | S | 1/2021 | Ach et al. |
| 10,881,911 | B2 | 1/2021 | Kwon et al. |
| 10,902,944 | B1 | 1/2021 | Casey |
| 10,918,332 | B2 | 2/2021 | Belson et al. |
| 10,931,643 | B1 | 2/2021 | Neumann |
| 10,987,176 | B2 | 4/2021 | Poltaretskyi et al. |
| 10,991,463 | B2 | 4/2021 | Kutzko et al. |
| 11,000,735 | B2 | 5/2021 | Orady et al. |
| 11,045,709 | B2 | 6/2021 | Putnam |
| 11,065,170 | B2 | 7/2021 | Yang et al. |
| 11,065,527 | B2 | 7/2021 | Putnam |
| 11,069,436 | B2 | 7/2021 | Mason et al. |
| 11,071,597 | B2 | 7/2021 | Posnack et al. |
| 11,075,000 | B2 | 7/2021 | Mason et al. |
| D928,635 | S | 8/2021 | Hacking et al. |
| 11,087,865 | B2 | 8/2021 | Mason et al. |
| 11,094,400 | B2 | 8/2021 | Riley et al. |
| 11,101,028 | B2 | 8/2021 | Mason et al. |
| 11,107,591 | B1 | 8/2021 | Mason |
| 11,139,060 | B2 | 10/2021 | Mason et al. |
| 11,185,735 | B2 | 11/2021 | Arn et al. |
| 11,185,738 | B1 | 11/2021 | McKirdy et al. |
| D939,096 | S | 12/2021 | Lee |

(56) References Cited

U.S. PATENT DOCUMENTS

| | | | |
|---|---|---|---|
| D939,644 S | 12/2021 | Ach et al. |
| D940,797 S | 1/2022 | Ach et al. |
| D940,891 S | 1/2022 | Lee |
| 11,229,727 B2 | 1/2022 | Tatonetti |
| 11,229,788 B1 | 1/2022 | John |
| 11,265,234 B2 | 3/2022 | Guaneri et al. |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,298,284 B2 | 4/2022 | Bayerlein |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,331,537 B1 | 5/2022 | Ketchell |
| 11,337,648 B2 | 5/2022 | Mason |
| 11,347,829 B1 | 5/2022 | Sclar et al. |
| 11,348,683 B2 | 5/2022 | Guaneri et al. |
| 11,370,328 B2 | 6/2022 | Main |
| 11,376,470 B2 | 7/2022 | Weldemariam |
| 11,404,150 B2 | 8/2022 | Guaneri et al. |
| 11,410,768 B2 | 8/2022 | Mason et al. |
| 11,422,841 B2 | 8/2022 | Jeong |
| 11,437,137 B1 | 9/2022 | Harris |
| 11,495,355 B2 | 11/2022 | McNutt et al. |
| 11,508,258 B2 | 11/2022 | Nakashima et al. |
| 11,508,482 B2 | 11/2022 | Mason et al. |
| 11,515,021 B2 | 11/2022 | Mason |
| 11,515,028 B2 | 11/2022 | Mason |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,541,274 B2 | 1/2023 | Hacking |
| 11,553,969 B1 | 1/2023 | Lang et al. |
| 11,621,067 B1 | 4/2023 | Nolan |
| 11,636,944 B2 | 4/2023 | Hanrahan et al. |
| 11,654,327 B2 | 5/2023 | Phillips et al. |
| 11,663,673 B2 | 5/2023 | Pyles |
| 11,673,024 B2 | 6/2023 | Omid-Zohoor |
| 11,701,548 B2 | 7/2023 | Posnack et al. |
| 11,756,666 B2 | 9/2023 | Rosenberg |
| 11,776,676 B2 | 10/2023 | Savolainen |
| 11,944,579 B2 | 4/2024 | Sankai |
| 11,957,960 B2 | 4/2024 | Bissonnette et al. |
| 12,004,871 B1 | 6/2024 | Fazeli |
| 12,020,511 B1 | 6/2024 | Denton et al. |
| 12,042,714 B1 | 7/2024 | Campbell |
| 12,057,210 B2 | 8/2024 | Akinola et al. |
| 12,176,091 B2 | 12/2024 | Rosenberg |
| 12,205,704 B2 | 1/2025 | Hosoi et al. |
| 2001/0044573 A1 | 11/2001 | Manoli |
| 2002/0010596 A1 | 1/2002 | Matory |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0064860 A1 | 4/2003 | Yamashita et al. |
| 2003/0064863 A1 | 4/2003 | Chen |
| 2003/0083596 A1 | 5/2003 | Kramer et al. |
| 2003/0092536 A1 | 5/2003 | Romanelli et al. |
| 2003/0181832 A1 | 9/2003 | Carnahan et al. |
| 2004/0072652 A1 | 4/2004 | Alessandri et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0197727 A1 | 10/2004 | Sachdeva et al. |
| 2004/0204959 A1 | 10/2004 | Moreano et al. |
| 2005/0015118 A1 | 1/2005 | Davis et al. |
| 2005/0020411 A1 | 1/2005 | Andrews |
| 2005/0043145 A1 | 2/2005 | Anderson |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0115561 A1 | 6/2005 | Stahmann |
| 2005/0143641 A1 | 6/2005 | Tashiro |
| 2005/0274220 A1 | 12/2005 | Reboullet |
| 2006/0003871 A1 | 1/2006 | Houghton et al. |
| 2006/0046905 A1 | 3/2006 | Doody, Jr. et al. |
| 2006/0058648 A1 | 3/2006 | Meier |
| 2006/0064136 A1 | 3/2006 | Wang |
| 2006/0064329 A1 | 3/2006 | Abolfathi et al. |
| 2006/0129432 A1 | 6/2006 | Choi et al. |
| 2006/0199700 A1 | 9/2006 | LaStayo et al. |
| 2006/0247095 A1 | 11/2006 | Rummerfield |
| 2006/0277074 A1 | 12/2006 | Einav |
| 2007/0042868 A1 | 2/2007 | Fisher et al. |
| 2007/0118389 A1 | 5/2007 | Shipon |
| 2007/0118406 A1 | 5/2007 | Killin et al. |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0271065 A1 | 11/2007 | Gupta et al. |
| 2007/0287597 A1 | 12/2007 | Cameron |
| 2008/0021834 A1 | 1/2008 | Holla et al. |
| 2008/0077619 A1 | 3/2008 | Gilley et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0183500 A1 | 7/2008 | Banigan |
| 2008/0281633 A1 | 11/2008 | Burdea et al. |
| 2008/0300914 A1 | 12/2008 | Karkanias et al. |
| 2008/0312040 A1 | 12/2008 | Ochi |
| 2008/0319330 A1 | 12/2008 | Juntunen |
| 2009/0011907 A1 | 1/2009 | Radow et al. |
| 2009/0037334 A1 | 2/2009 | Hsu |
| 2009/0058635 A1 | 3/2009 | LaLonde et al. |
| 2009/0070138 A1 | 3/2009 | Langheier et al. |
| 2009/0157617 A1 | 6/2009 | Herlocker |
| 2009/0211395 A1 | 8/2009 | Mule |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0062818 A1 | 3/2010 | Haughay, Jr. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0248905 A1 | 9/2010 | Lu |
| 2010/0262052 A1 | 10/2010 | Lunau et al. |
| 2010/0268304 A1 | 10/2010 | Matos |
| 2010/0293003 A1 | 11/2010 | Abbo |
| 2010/0298102 A1 | 11/2010 | Bosecker et al. |
| 2010/0326207 A1 | 12/2010 | Topel |
| 2010/0332583 A1 | 12/2010 | Szabo |
| 2011/0010188 A1 | 1/2011 | Yoshikawa et al. |
| 2011/0047108 A1 | 2/2011 | Chakrabarty et al. |
| 2011/0082007 A1 | 4/2011 | Birrell |
| 2011/0087137 A1 | 4/2011 | Hanoun |
| 2011/0119212 A1* | 5/2011 | De Bruin .............. A61B 5/369 |
| | | 706/12 |
| 2011/0172059 A1 | 7/2011 | Watterson et al. |
| 2011/0195819 A1 | 8/2011 | Shaw et al. |
| 2011/0218462 A1 | 9/2011 | Smith |
| 2011/0218814 A1 | 9/2011 | Coats |

(56) References Cited

U.S. PATENT DOCUMENTS

| | | | |
|---|---|---|---|
| 2011/0275483 A1 | 11/2011 | Dugan |
| 2011/0281249 A1 | 11/2011 | Gammell et al. |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0130196 A1 | 5/2012 | Jain et al. |
| 2012/0130197 A1 | 5/2012 | Kugler et al. |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0248346 A1 | 10/2012 | Chowdhary |
| 2012/0259648 A1 | 10/2012 | Mallon et al. |
| 2012/0259649 A1 | 10/2012 | Mallon et al. |
| 2012/0278759 A1 | 11/2012 | Curl et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0066647 A1 | 3/2013 | Andrie |
| 2013/0079925 A1 | 3/2013 | Alaklabi et al. |
| 2013/0083054 A1 | 4/2013 | Bayouk |
| 2013/0108594 A1 | 5/2013 | Martin-Rendon et al. |
| 2013/0110545 A1 | 5/2013 | Smallwood |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0137552 A1 | 5/2013 | Kemp et al. |
| 2013/0158368 A1 | 6/2013 | Pacione |
| 2013/0165195 A1 | 6/2013 | Watterson |
| 2013/0171599 A1 | 7/2013 | Bleich |
| 2013/0173305 A1 | 7/2013 | Hyde |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0031174 A1 | 1/2014 | Huang |
| 2014/0038781 A1 | 2/2014 | Foley et al. |
| 2014/0062900 A1 | 3/2014 | Kaula et al. |
| 2014/0074179 A1 | 3/2014 | Heldman et al. |
| 2014/0089836 A1 | 3/2014 | Damani et al. |
| 2014/0108035 A1 | 4/2014 | Akbay |
| 2014/0113261 A1 | 4/2014 | Akiba |
| 2014/0113768 A1 | 4/2014 | Lin et al. |
| 2014/0135173 A1 | 5/2014 | Watterson |
| 2014/0155129 A1 | 6/2014 | Dugan |
| 2014/0163439 A1 | 6/2014 | Uryash et al. |
| 2014/0172442 A1 | 6/2014 | Broderick |
| 2014/0172460 A1 | 6/2014 | Kohli |
| 2014/0172514 A1 | 6/2014 | Schumann et al. |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0200414 A1 | 7/2014 | Osorio |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0275816 A1 | 9/2014 | Sandmore |
| 2014/0303540 A1 | 10/2014 | Baym |
| 2014/0309083 A1 | 10/2014 | Dugan |
| 2014/0322686 A1 | 10/2014 | Kang |
| 2014/0347265 A1 | 11/2014 | Aimone et al. |
| 2014/0371816 A1 | 12/2014 | Matos |
| 2014/0372133 A1 | 12/2014 | Austrum et al. |
| 2015/0025816 A1 | 1/2015 | Ross |
| 2015/0045700 A1 | 2/2015 | Cavanagh et al. |
| 2015/0046192 A1 | 2/2015 | Raduchel |
| 2015/0051721 A1 | 2/2015 | Cheng |
| 2015/0065213 A1 | 3/2015 | Dugan |
| 2015/0073814 A1 | 3/2015 | Linebaugh |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0111644 A1 | 4/2015 | Larson |
| 2015/0112230 A1 | 4/2015 | Iglesias |
| 2015/0112702 A1 | 4/2015 | Joao et al. |
| 2015/0130830 A1 | 5/2015 | Nagasaki |
| 2015/0141200 A1 | 5/2015 | Murray et al. |
| 2015/0142142 A1 | 5/2015 | Aguilera et al. |
| 2015/0149217 A1 | 5/2015 | Kaburagi |
| 2015/0151162 A1 | 6/2015 | Dugan |
| 2015/0157918 A1 | 6/2015 | Tracy |
| 2015/0157938 A1 | 6/2015 | Domansky et al. |
| 2015/0161331 A1 | 6/2015 | Oleynik |
| 2015/0161876 A1 | 6/2015 | Castillo |
| 2015/0174446 A1 | 6/2015 | Chiang |
| 2015/0196804 A1 | 7/2015 | Koduri |
| 2015/0196805 A1 | 7/2015 | Koduri |
| 2015/0199494 A1 | 7/2015 | Koduri |
| 2015/0217056 A1 | 8/2015 | Kadavy et al. |
| 2015/0251074 A1 | 9/2015 | Ahmed et al. |
| 2015/0257679 A1 | 9/2015 | Ross |
| 2015/0265209 A1 | 9/2015 | Zhang |
| 2015/0273272 A1 | 10/2015 | Wang |
| 2015/0290061 A1 | 10/2015 | Stafford et al. |
| 2015/0331997 A1 | 11/2015 | Joao |
| 2015/0335950 A1 | 11/2015 | Eder |
| 2015/0335951 A1 | 11/2015 | Eder |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0359467 A1 | 12/2015 | Tran |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0004820 A1 | 1/2016 | Moore |
| 2016/0007885 A1 | 1/2016 | Basta |
| 2016/0009338 A1 | 1/2016 | Biderman |
| 2016/0015995 A1 | 1/2016 | Leung et al. |
| 2016/0023081 A1 | 1/2016 | Popa-Simil et al. |
| 2016/0045170 A1 | 2/2016 | Migita |
| 2016/0081594 A1 | 3/2016 | Gaddipati |
| 2016/0084869 A1 | 3/2016 | Yuen |
| 2016/0086500 A1 | 3/2016 | Kaleal, III |
| 2016/0096073 A1 | 4/2016 | Rahman et al. |
| 2016/0117471 A1 | 4/2016 | Belt et al. |
| 2016/0132643 A1 | 5/2016 | Radhakrishna et al. |
| 2016/0140319 A1 | 5/2016 | Stark |
| 2016/0143593 A1 | 5/2016 | Fu et al. |
| 2016/0151670 A1 | 6/2016 | Dugan |
| 2016/0158534 A1 | 6/2016 | Guarraia et al. |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0197918 A1 | 7/2016 | Turgeman et al. |
| 2016/0213924 A1 | 7/2016 | Coleman |
| 2016/0232321 A1 | 8/2016 | Silverman |
| 2016/0250519 A1 | 9/2016 | Watterson |
| 2016/0275259 A1 | 9/2016 | Nolan et al. |
| 2016/0287166 A1 | 10/2016 | Tran |
| 2016/0294837 A1 | 10/2016 | Turgeman |
| 2016/0302666 A1 | 10/2016 | Shaya |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0345841 A1 | 12/2016 | Jang et al. |
| 2016/0354636 A1 | 12/2016 | Jang |
| 2016/0361025 A1 | 12/2016 | Reicher et al. |
| 2016/0361597 A1 | 12/2016 | Cole et al. |

(56) References Cited

U.S. PATENT DOCUMENTS

| 2016/0373477 | A1 | 12/2016 | Moyle |
| 2017/0000422 | A1 | 1/2017 | Moturu et al. |
| 2017/0004260 | A1 | 1/2017 | Moturu et al. |
| 2017/0011179 | A1 | 1/2017 | Arshad et al. |
| 2017/0032092 | A1 | 2/2017 | Mink et al. |
| 2017/0033375 | A1 | 2/2017 | Ohmori et al. |
| 2017/0042467 | A1 | 2/2017 | Herr et al. |
| 2017/0043160 | A1 | 2/2017 | Goodall et al. |
| 2017/0046488 | A1 | 2/2017 | Pereira |
| 2017/0065851 | A1 | 3/2017 | Deluca et al. |
| 2017/0069223 | A1 | 3/2017 | Cramer et al. |
| 2017/0080281 | A1 | 3/2017 | Hartman |
| 2017/0080320 | A1 | 3/2017 | Smith |
| 2017/0091422 | A1 | 3/2017 | Kumar et al. |
| 2017/0095670 | A1 | 4/2017 | Ghaffari et al. |
| 2017/0095692 | A1 | 4/2017 | Chang et al. |
| 2017/0095693 | A1 | 4/2017 | Chang et al. |
| 2017/0100637 | A1 | 4/2017 | Princen et al. |
| 2017/0106242 | A1 | 4/2017 | Dugan |
| 2017/0113092 | A1 | 4/2017 | Johnson |
| 2017/0128769 | A1 | 5/2017 | Long et al. |
| 2017/0132947 | A1 | 5/2017 | Maeda et al. |
| 2017/0136296 | A1 | 5/2017 | Barrera et al. |
| 2017/0136297 | A1 | 5/2017 | Penie |
| 2017/0136298 | A1 | 5/2017 | Bae |
| 2017/0143261 | A1 | 5/2017 | Wiedenhoefer et al. |
| 2017/0143262 | A1 | 5/2017 | Kurunmaki |
| 2017/0147752 | A1 | 5/2017 | Toru |
| 2017/0147789 | A1 | 5/2017 | Wiedenhoefer et al. |
| 2017/0148297 | A1 | 5/2017 | Ross |
| 2017/0168555 | A1 | 6/2017 | Munoz et al. |
| 2017/0169177 | A1 | 6/2017 | Beale |
| 2017/0173391 | A1 | 6/2017 | Wiebe |
| 2017/0181698 | A1 | 6/2017 | Wiedenhoefer et al. |
| 2017/0190052 | A1 | 7/2017 | Jaekel et al. |
| 2017/0200264 | A1 | 7/2017 | Park |
| 2017/0202724 | A1 | 7/2017 | De Rossi |
| 2017/0209766 | A1 | 7/2017 | Riley et al. |
| 2017/0220751 | A1 | 8/2017 | Davis |
| 2017/0228517 | A1 | 8/2017 | Saliman et al. |
| 2017/0235882 | A1 | 8/2017 | Orlov et al. |
| 2017/0235906 | A1 | 8/2017 | Dorris et al. |
| 2017/0243028 | A1 | 8/2017 | LaFever et al. |
| 2017/0258370 | A1 | 9/2017 | Plotnik-Peleg et al. |
| 2017/0262604 | A1 | 9/2017 | Francois |
| 2017/0265800 | A1 | 9/2017 | Auchinleck et al. |
| 2017/0266501 | A1 | 9/2017 | Sanders et al. |
| 2017/0270260 | A1 | 9/2017 | Shetty |
| 2017/0278209 | A1 | 9/2017 | Olsen et al. |
| 2017/0282015 | A1 | 10/2017 | Wicks et al. |
| 2017/0283508 | A1 | 10/2017 | Demopulos et al. |
| 2017/0286621 | A1 | 10/2017 | Cox |
| 2017/0291067 | A1 | 10/2017 | Jang et al. |
| 2017/0296861 | A1 | 10/2017 | Burkinshaw |
| 2017/0300654 | A1 | 10/2017 | Stein et al. |
| 2017/0304024 | A1 | 10/2017 | Nobrega |
| 2017/0312614 | A1 | 11/2017 | Tran et al. |
| 2017/0323481 | A1 | 11/2017 | Tran et al. |
| 2017/0329917 | A1 | 11/2017 | McRaith et al. |
| 2017/0329933 | A1 | 11/2017 | Brust |
| 2017/0333755 | A1 | 11/2017 | Rider |
| 2017/0337033 | A1 | 11/2017 | Duyan et al. |
| 2017/0337334 | A1 | 11/2017 | Stanczak |
| 2017/0344726 | A1 | 11/2017 | Duffy et al. |
| 2017/0347923 | A1 | 12/2017 | Roh |
| 2017/0352157 | A1 | 12/2017 | Madabhushi |
| 2017/0360586 | A1 | 12/2017 | Dempers et al. |
| 2017/0361165 | A1 | 12/2017 | Miller et al. |
| 2017/0367606 | A1 | 12/2017 | Lee |
| 2017/0368413 | A1 | 12/2017 | Shavit |
| 2018/0017806 | A1 | 1/2018 | Wang et al. |
| 2018/0036591 | A1 | 2/2018 | King et al. |
| 2018/0036593 | A1 | 2/2018 | Ridgel et al. |
| 2018/0052962 | A1 | 2/2018 | Van Der Koijk et al. |
| 2018/0052968 | A1 | 2/2018 | Hickle et al. |
| 2018/0056104 | A1 | 3/2018 | Cromie et al. |
| 2018/0056130 | A1 | 3/2018 | Bitran et al. |
| 2018/0060494 | A1 | 3/2018 | Dias et al. |
| 2018/0070864 | A1 | 3/2018 | Schuster |
| 2018/0071565 | A1 | 3/2018 | Gomberg et al. |
| 2018/0071566 | A1 | 3/2018 | Gomberg et al. |
| 2018/0071569 | A1 | 3/2018 | Gomberg et al. |
| 2018/0071570 | A1 | 3/2018 | Gomberg et al. |
| 2018/0071571 | A1 | 3/2018 | Gomberg et al. |
| 2018/0071572 | A1 | 3/2018 | Gomberg et al. |
| 2018/0075205 | A1 | 3/2018 | Moturu et al. |
| 2018/0078149 | A1 | 3/2018 | Fonte et al. |
| 2018/0078182 | A1 | 3/2018 | Chen |
| 2018/0078843 | A1 | 3/2018 | Tran et al. |
| 2018/0085615 | A1 | 3/2018 | Astolfi et al. |
| 2018/0089385 | A1 | 3/2018 | Gupta |
| 2018/0096111 | A1 | 4/2018 | Wells et al. |
| 2018/0099178 | A1 | 4/2018 | Schaefer et al. |
| 2018/0102190 | A1 | 4/2018 | Hogue et al. |
| 2018/0103859 | A1 | 4/2018 | Provenzano |
| 2018/0113985 | A1 | 4/2018 | Gandy et al. |
| 2018/0116741 | A1 | 5/2018 | Garcia Kilroy et al. |
| 2018/0117417 | A1 | 5/2018 | Davis |
| 2018/0130555 | A1 | 5/2018 | Chronis et al. |
| 2018/0133551 | A1 | 5/2018 | Chang |
| 2018/0140927 | A1 | 5/2018 | Kito |
| 2018/0146870 | A1 | 5/2018 | Shemesh |
| 2018/0169476 | A1 | 6/2018 | Shimada |
| 2018/0177612 | A1 | 6/2018 | Trabish et al. |
| 2018/0178061 | A1 | 6/2018 | O'larte et al. |
| 2018/0199855 | A1 | 7/2018 | Odame et al. |
| 2018/0200577 | A1 | 7/2018 | Dugan |
| 2018/0220935 | A1 | 8/2018 | Tadano et al. |
| 2018/0228682 | A1 | 8/2018 | Bayerlein et al. |
| 2018/0232492 | A1 | 8/2018 | Al-Alul et al. |
| 2018/0236307 | A1 | 8/2018 | Hyde et al. |
| 2018/0240552 | A1 | 8/2018 | Tuyl et al. |
| 2018/0250075 | A1* | 9/2018 | Cho ........................ A61B 34/10 |
| 2018/0253991 | A1 | 9/2018 | Tang et al. |
| 2018/0255110 | A1 | 9/2018 | Dowlatkhah et al. |
| 2018/0256079 | A1 | 9/2018 | Yang et al. |
| 2018/0256939 | A1 | 9/2018 | Malcolm |
| 2018/0263530 | A1 | 9/2018 | Jung |
| 2018/0263535 | A1 | 9/2018 | Cramer |
| 2018/0263552 | A1 | 9/2018 | Graman et al. |
| 2018/0264312 | A1 | 9/2018 | Pompile et al. |
| 2018/0271432 | A1 | 9/2018 | Auchinleck et al. |
| 2018/0272184 | A1 | 9/2018 | Vassilaros et al. |
| 2018/0272190 | A1 | 9/2018 | Miura |
| 2018/0280784 | A1 | 10/2018 | Romeo et al. |
| 2018/0285463 | A1 | 10/2018 | Choi et al. |
| 2018/0290017 | A1 | 10/2018 | Fung |
| 2018/0296143 | A1 | 10/2018 | Anderson et al. |
| 2018/0296157 | A1 | 10/2018 | Bleich et al. |
| 2018/0318122 | A1 | 11/2018 | LeCursi et al. |
| 2018/0326243 | A1 | 11/2018 | Badi et al. |
| 2018/0330058 | A1 | 11/2018 | Bates |
| 2018/0330810 | A1 | 11/2018 | Gamarnik |
| 2018/0330824 | A1 | 11/2018 | Athey et al. |
| 2018/0348759 | A1 | 12/2018 | Freeman |
| 2018/0353812 | A1 | 12/2018 | Lannon et al. |
| 2018/0358119 | A1 | 12/2018 | Bhushan |
| 2018/0360340 | A1 | 12/2018 | Rehse et al. |
| 2018/0361203 | A1 | 12/2018 | Wang |
| 2018/0366225 | A1 | 12/2018 | Mansi et al. |
| 2018/0373844 | A1 | 12/2018 | Ferrandez-Escamez et al. |
| 2019/0005195 | A1 | 1/2019 | Peterson |
| 2019/0009135 | A1 | 1/2019 | Wu |
| 2019/0009136 | A1 | 1/2019 | Lee |
| 2019/0019163 | A1 | 1/2019 | Batey et al. |
| 2019/0019573 | A1 | 1/2019 | Lake et al. |
| 2019/0019578 | A1 | 1/2019 | Vaccaro |
| 2019/0025995 | A1 | 1/2019 | Williams |
| 2019/0030415 | A1 | 1/2019 | Volpe, Jr. |
| 2019/0031284 | A1 | 1/2019 | Fuchs |
| 2019/0046794 | A1 | 2/2019 | Goodall et al. |
| 2019/0060708 | A1 | 2/2019 | Fung |
| 2019/0065970 | A1 | 2/2019 | Bonutti et al. |
| 2019/0066832 | A1 | 2/2019 | Kang et al. |

(56) References Cited

U.S. PATENT DOCUMENTS

| | | |
|---|---|---|
| 2019/0076701 A1 | 3/2019 | Dugan |
| 2019/0080802 A1 | 3/2019 | Ziobro et al. |
| 2019/0083846 A1 | 3/2019 | Eder |
| 2019/0088356 A1 | 3/2019 | Oliver et al. |
| 2019/0090744 A1 | 3/2019 | Mahfouz |
| 2019/0096534 A1 | 3/2019 | Joao |
| 2019/0105551 A1 | 4/2019 | Ray |
| 2019/0108912 A1 | 4/2019 | Spurlock, III |
| 2019/0111299 A1 | 4/2019 | Radcliffe et al. |
| 2019/0115097 A1 | 4/2019 | Macoviak et al. |
| 2019/0117156 A1 | 4/2019 | Howard et al. |
| 2019/0118038 A1 | 4/2019 | Tana et al. |
| 2019/0118066 A1 | 4/2019 | Cardona |
| 2019/0122770 A1 | 4/2019 | Pengetnze |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0143191 A1 | 5/2019 | Ran et al. |
| 2019/0143193 A1 | 5/2019 | Kim |
| 2019/0145774 A1 | 5/2019 | Ellis |
| 2019/0146740 A1 | 5/2019 | Yuen |
| 2019/0163876 A1 | 5/2019 | Remme et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0192880 A1 | 6/2019 | Hibbard |
| 2019/0200920 A1 | 7/2019 | Tien et al. |
| 2019/0209022 A1* | 7/2019 | Sobol .................... A61B 5/681 |
| 2019/0209891 A1 | 7/2019 | Fung |
| 2019/0214119 A1 | 7/2019 | Wachira et al. |
| 2019/0223797 A1 | 7/2019 | Tran |
| 2019/0224528 A1 | 7/2019 | Omid-Zohoor et al. |
| 2019/0228856 A1 | 7/2019 | Leifer |
| 2019/0232108 A1 | 8/2019 | Kovach et al. |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0247718 A1 | 8/2019 | Blevins |
| 2019/0251456 A1 | 8/2019 | Constantin |
| 2019/0251723 A1 | 8/2019 | Coppersmith |
| 2019/0261959 A1 | 8/2019 | Frankel |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0283247 A1 | 9/2019 | Chang |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0371472 A1 | 12/2019 | Blanchard |
| 2019/0385199 A1 | 12/2019 | Bender et al. |
| 2019/0388728 A1 | 12/2019 | Wang et al. |
| 2019/0392936 A1 | 12/2019 | Arric et al. |
| 2019/0392939 A1 | 12/2019 | Basta et al. |
| 2020/0005928 A1 | 1/2020 | Daniel |
| 2020/0015736 A1 | 1/2020 | Alhathal |
| 2020/0034665 A1 | 1/2020 | Ghanta |
| 2020/0034707 A1 | 1/2020 | Kivatinos et al. |
| 2020/0038703 A1 | 2/2020 | Cleary et al. |
| 2020/0051446 A1 | 2/2020 | Rubinstein |
| 2020/0054922 A1 | 2/2020 | Azaria |
| 2020/0066390 A1 | 2/2020 | Svendrys et al. |
| 2020/0085300 A1 | 3/2020 | Kwatra et al. |
| 2020/0090802 A1 | 3/2020 | Maron |
| 2020/0093418 A1 | 3/2020 | Kluger et al. |
| 2020/0098463 A1 | 3/2020 | Arunachalam et al. |
| 2020/0121987 A1 | 4/2020 | Loh |
| 2020/0129808 A1 | 4/2020 | Fomin |
| 2020/0139194 A1 | 5/2020 | Min |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0188774 A1 | 6/2020 | Fung |
| 2020/0197744 A1 | 6/2020 | Schweighofer |
| 2020/0221975 A1 | 7/2020 | Basta et al. |
| 2020/0237291 A1 | 7/2020 | Raja |
| 2020/0237452 A1 | 7/2020 | Wolf et al. |
| 2020/0261763 A1 | 8/2020 | Park |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0312447 A1 | 10/2020 | Bohn et al. |
| 2020/0320454 A1 | 10/2020 | Almashor |
| 2020/0334972 A1 | 10/2020 | Gopalakrishnan |
| 2020/0338394 A1 | 10/2020 | Neumann |
| 2020/0346072 A1 | 11/2020 | Shah |
| 2020/0350076 A1 | 11/2020 | Brown |
| 2020/0353314 A1 | 11/2020 | Messinger |
| 2020/0357299 A1 | 11/2020 | Patel et al. |
| 2020/0365256 A1 | 11/2020 | Hayashitani et al. |
| 2020/0391080 A1 | 12/2020 | Powers |
| 2020/0395112 A1 | 12/2020 | Ronner |
| 2020/0398083 A1 | 12/2020 | Adelsheim |
| 2020/0401224 A1 | 12/2020 | Cotton |
| 2020/0402638 A1 | 12/2020 | Song et al. |
| 2020/0402662 A1 | 12/2020 | Esmailian et al. |
| 2020/0410374 A1 | 12/2020 | White |
| 2020/0410385 A1 | 12/2020 | Otsuki |
| 2020/0410893 A1 | 12/2020 | Ridington |
| 2020/0411162 A1 | 12/2020 | Lien et al. |
| 2020/0411170 A1 | 12/2020 | Brown |
| 2021/0005224 A1 | 1/2021 | Rothschild et al. |
| 2021/0005319 A1 | 1/2021 | Otsuki et al. |
| 2021/0008413 A1 | 1/2021 | Asikainen et al. |
| 2021/0015560 A1 | 1/2021 | Boddington et al. |
| 2021/0027889 A1 | 1/2021 | Neil et al. |
| 2021/0035674 A1 | 2/2021 | Volosin et al. |
| 2021/0050086 A1 | 2/2021 | Rose et al. |
| 2021/0065855 A1 | 3/2021 | Pepin et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0077884 A1 | 3/2021 | De Las Casas Zolezzi et al. |
| 2021/0082554 A1 | 3/2021 | Kalia et al. |
| 2021/0093891 A1 | 4/2021 | Sheng |
| 2021/0098099 A1 | 4/2021 | Neumann |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0125696 A1 | 4/2021 | Liu et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134427 A1 | 5/2021 | Mason et al. |
| 2021/0134428 A1 | 5/2021 | Mason |
| 2021/0134429 A1 | 5/2021 | Mason |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |

(56) References Cited

U.S. PATENT DOCUMENTS

| | | |
|---|---|---|
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0187348 A1 | 6/2021 | Phillips et al. |
| 2021/0202090 A1 | 7/2021 | ODonovan et al. |
| 2021/0202103 A1 | 7/2021 | Bostic et al. |
| 2021/0205660 A1 | 7/2021 | Shavit |
| 2021/0217516 A1 | 7/2021 | Nash |
| 2021/0236020 A1 | 8/2021 | Matijevich et al. |
| 2021/0236903 A1 | 8/2021 | Briel |
| 2021/0240853 A1 | 8/2021 | Carlson |
| 2021/0241137 A1 | 8/2021 | Jain et al. |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0354002 A1 | 11/2021 | Schaefer |
| 2021/0361514 A1 | 11/2021 | Choi et al. |
| 2021/0366587 A1 | 11/2021 | Mason et al. |
| 2021/0369536 A1 | 12/2021 | Mooney |
| 2021/0375425 A1 | 12/2021 | Zhang |
| 2021/0383008 A1 | 12/2021 | Manasse |
| 2021/0383909 A1 | 12/2021 | Mason et al. |
| 2021/0387054 A1 | 12/2021 | Schaefer |
| 2021/0391091 A1 | 12/2021 | Mason |
| 2021/0394011 A1 | 12/2021 | Neuhaus et al. |
| 2021/0398668 A1 | 12/2021 | Chock et al. |
| 2021/0406738 A1 | 12/2021 | O'Donncha et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack |
| 2022/0016480 A1 | 1/2022 | Bissonnette et al. |
| 2022/0016482 A1 | 1/2022 | Bissonnette |
| 2022/0016484 A1 | 1/2022 | Bissonnett et al. |
| 2022/0016485 A1 | 1/2022 | Bissonnette |
| 2022/0016486 A1 | 1/2022 | Bissonnette et al. |
| 2022/0020469 A1 | 1/2022 | Tanner |
| 2022/0044806 A1 | 2/2022 | Sanders et al. |
| 2022/0047921 A1 | 2/2022 | Bissonnette |
| 2022/0066548 A1 | 3/2022 | Helot |
| 2022/0079690 A1 | 3/2022 | Mason et al. |
| 2022/0080256 A1 | 3/2022 | Arn et al. |
| 2022/0080265 A1 | 3/2022 | Watterson |
| 2022/0096006 A1 | 3/2022 | Wu et al. |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0117514 A1 | 4/2022 | Kuhn et al. |
| 2022/0118218 A1 | 4/2022 | Bense et al. |
| 2022/0122724 A1 | 4/2022 | Durlach et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0165398 A1 | 5/2022 | Avila-Hernandez et al. |
| 2022/0176039 A1 | 6/2022 | Lintereur et al. |
| 2022/0181004 A1 | 6/2022 | Zilca et al. |
| 2022/0193491 A1 | 6/2022 | Mason |
| 2022/0230729 A1 | 7/2022 | Mason et al. |
| 2022/0238222 A1 | 7/2022 | Neuberg |
| 2022/0238223 A1 | 7/2022 | Mason |
| 2022/0258935 A1 | 8/2022 | Kraft |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305291 A1 | 9/2022 | Hibbard |
| 2022/0305328 A1 | 9/2022 | Choi et al. |
| 2022/0314072 A1 | 10/2022 | Bissonnette et al. |
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0336077 A1 | 10/2022 | Chen et al. |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0342969 A1 | 10/2022 | Watterson et al. |
| 2022/0346703 A1 | 11/2022 | Abdo et al. |
| 2022/0370851 A1 | 11/2022 | Guidarelli et al. |
| 2022/0384010 A1 | 12/2022 | Kanayama |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0022981 A1 | 1/2023 | Bhushan |
| 2023/0029639 A1 | 2/2023 | Roy |
| 2023/0047253 A1 | 2/2023 | Gnanasambandam et al. |
| 2023/0048040 A1 | 2/2023 | Hacking et al. |
| 2023/0051751 A1 | 2/2023 | Hacking et al. |
| 2023/0055078 A1 | 2/2023 | Malcolm |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0197240 A1 | 6/2023 | Rosenberg |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0218950 A1 | 7/2023 | Belson et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0249599 A1 | 8/2023 | Nicola |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364471 A1 | 11/2023 | Choi et al. |
| 2023/0364472 A1 | 11/2023 | Posnack |
| 2023/0368886 A1 | 11/2023 | Rosenberg |
| 2023/0377710 A1 | 11/2023 | Chen et al. |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0390627 A1 | 12/2023 | Bolton |

(56) References Cited

U.S. PATENT DOCUMENTS

| | | | |
|---|---|---|---|
| 2023/0395231 A1 | 12/2023 | Rosenberg |
| 2023/0395232 A1 | 12/2023 | Rosenberg |
| 2024/0029856 A1 | 1/2024 | Rosenberg |
| 2024/0058651 A1 | 2/2024 | Bissonnette |
| 2024/0177846 A1 | 5/2024 | Gnanasambandam |
| 2024/0203580 A1 | 6/2024 | Mason |

FOREIGN PATENT DOCUMENTS

| | | | |
|---|---|---|---|
| CN | 101964151 | A | 2/2011 |
| CN | 201889024 | U | 7/2011 |
| CN | 202220794 | U | 5/2012 |
| CN | 102670381 | A | 9/2012 |
| CN | 103263336 | A | 8/2013 |
| CN | 103390357 | A | 11/2013 |
| CN | 103473631 | A | 12/2013 |
| CN | 103488880 | A | 1/2014 |
| CN | 103501328 | A | 1/2014 |
| CN | 103721343 | A | 4/2014 |
| CN | 203677851 | U | 7/2014 |
| CN | 104335211 | A | 2/2015 |
| CN | 105263448 | A | 1/2016 |
| CN | 105620643 | A | 6/2016 |
| CN | 105683977 | A | 6/2016 |
| CN | 103136447 | B | 8/2016 |
| CN | 105894088 | A | 8/2016 |
| CN | 105930668 | A | 9/2016 |
| CN | 205626871 | U | 10/2016 |
| CN | 106127646 | A | 11/2016 |
| CN | 106236502 | A | 12/2016 |
| CN | 106510985 | A | 3/2017 |
| CN | 106621195 | A | 5/2017 |
| CN | 106845077 | A | 6/2017 |
| CN | 107066819 | A | 8/2017 |
| CN | 107430641 | A | 12/2017 |
| CN | 107551475 | A | 1/2018 |
| CN | 107736982 | A | 2/2018 |
| CN | 107930021 | A | 4/2018 |
| CN | 108078737 | A | 5/2018 |
| CN | 208224811 | A | 12/2018 |
| CN | 109191954 | A | 1/2019 |
| CN | 109363887 | A | 2/2019 |
| CN | 208573971 | U | 3/2019 |
| CN | 110148472 | A | 8/2019 |
| CN | 110201358 | A | 9/2019 |
| CN | 110215188 | A | 9/2019 |
| CN | 110322957 | A | 10/2019 |
| CN | 110808092 | A | 2/2020 |
| CN | 110931103 | A | 3/2020 |
| CN | 110993057 | A | 4/2020 |
| CN | 111105859 | A | 5/2020 |
| CN | 111111110 | A | 5/2020 |
| CN | 111370088 | A | 7/2020 |
| CN | 111460305 | A | 7/2020 |
| CN | 111790111 | A | 10/2020 |
| CN | 112071393 | A | 12/2020 |
| CN | 212141371 | U | 12/2020 |
| CN | 112289425 | A | 1/2021 |
| CN | 212624809 | U | 2/2021 |
| CN | 112603295 | A | 4/2021 |
| CN | 213190965 | U | 5/2021 |
| CN | 113384850 | A | 9/2021 |
| CN | 113499572 | A | 10/2021 |
| CN | 215136488 | U | 12/2021 |
| CN | 113885361 | A | 1/2022 |
| CN | 114049961 | A | 2/2022 |
| CN | 114203274 | A | 3/2022 |
| CN | 216258145 | U | 4/2022 |
| CN | 114632302 | A | 6/2022 |
| CN | 114694824 | A | 7/2022 |
| CN | 114898832 | A | 8/2022 |
| CN | 114983760 | A | 9/2022 |
| CN | 217472652 | U | 9/2022 |
| CN | 110270062 | B | 10/2022 |
| CN | 218420859 | U | 2/2023 |
| CN | 115954081 | A | 4/2023 |
| DE | 95019 | C | 1/1897 |
| DE | 7628633 | U1 | 12/1977 |
| DE | 8519150 | U1 | 10/1985 |
| DE | 3732905 | A1 | 7/1988 |
| DE | 19619820 | A1 | 12/1996 |
| DE | 29620008 | U1 | 2/1997 |
| DE | 19947926 | A1 | 4/2001 |
| DE | 102018202497 | A1 | 8/2018 |
| DE | 102018211212 | A1 | 1/2019 |
| DE | 102019108425 | B3 | 8/2020 |
| EP | 199600 | A2 | 10/1986 |
| EP | 0383137 | A2 | 8/1990 |
| EP | 634319 | A2 | 1/1995 |
| EP | 0919259 | A1 | 6/1999 |
| EP | 1034817 | A1 | 9/2000 |
| EP | 1159989 | A1 | 12/2001 |
| EP | 1391179 | A1 | 2/2004 |
| EP | 1968028 | | 9/2008 |
| EP | 2564904 | A1 | 3/2013 |
| EP | 2575064 | A1 | 4/2013 |
| EP | 1909730 | B1 | 4/2014 |
| EP | 2815242 | A4 | 12/2014 |
| EP | 2869805 | A | 5/2015 |
| EP | 2997951 | A1 | 3/2016 |
| EP | 2688472 | B1 | 4/2016 |
| EP | 3264303 | A1 | 1/2018 |
| EP | 3323473 | A1 | 5/2018 |
| EP | 3547322 | A1 | 10/2019 |
| EP | 3627514 | A1 | 3/2020 |
| EP | 3671700 | A1 | 6/2020 |
| EP | 3688537 | A1 | 8/2020 |
| EP | 3731733 | A1 | 11/2020 |
| EP | 3984508 | A1 | 4/2022 |
| EP | 3984509 | A1 | 4/2022 |
| EP | 3984510 | A1 | 4/2022 |
| EP | 3984511 | A1 | 4/2022 |
| EP | 3984512 | A1 | 4/2022 |
| EP | 3984513 | A1 | 4/2022 |
| EP | 4054699 | A1 | 9/2022 |
| EP | 4112033 | A1 | 1/2023 |
| FR | 2527541 | A2 | 12/1983 |
| FR | 3127393 | A1 | 3/2023 |
| GB | 141664 | A | 11/1920 |
| GB | 2336140 | A | 10/1999 |
| GB | 2372459 | A | 8/2002 |
| GB | 2512431 | A | 10/2014 |
| GB | 2591542 | B | 3/2022 |
| IN | 201811043670 | A | 7/2018 |
| JP | 2000005339 | A | 1/2000 |
| JP | 2003225875 | A | 8/2003 |
| JP | 2005227928 | A | 8/2005 |
| JP | 2005227928 | A1 | 8/2005 |
| JP | 2009112336 | A | 5/2009 |
| JP | 2013515995 | A | 5/2013 |
| JP | 2014104139 | A | 6/2014 |
| JP | 3193662 | U | 10/2014 |
| JP | 3198173 | U | 6/2015 |
| JP | 5804063 | B2 | 11/2015 |
| JP | 2018102842 | A | 7/2018 |
| JP | 2019028647 | A | 2/2019 |
| JP | 2019134909 | A | 8/2019 |
| JP | 6573739 | B1 | 9/2019 |
| JP | 6659831 | B2 | 3/2020 |
| JP | 2020057082 | A | 4/2020 |
| JP | 6710357 | B1 | 6/2020 |
| JP | 6775757 | B1 | 10/2020 |
| JP | 2021027917 | A | 2/2021 |
| JP | 6871379 | B2 | 5/2021 |
| JP | 2022521378 | A | 4/2022 |
| JP | 3238491 | U | 7/2022 |
| JP | 7198364 | B2 | 12/2022 |
| JP | 7202474 | B2 | 1/2023 |
| JP | 7231750 | B2 | 3/2023 |
| JP | 7231751 | B2 | 3/2023 |
| JP | 7231752 | B2 | 3/2023 |
| KR | 20020009724 | A | 2/2002 |
| KR | 200276919 | Y1 | 5/2002 |
| KR | 20020065253 | A | 8/2002 |

(56) References Cited

FOREIGN PATENT DOCUMENTS

| | | | |
|---|---|---|---|
| KR | 100582596 | B1 | 5/2006 |
| KR | 101042258 | B1 | 6/2011 |
| KR | 101258250 | B1 | 4/2013 |
| KR | 101325581 | B1 | 11/2013 |
| KR | 20140128630 | A | 11/2014 |
| KR | 20150017693 | A | 2/2015 |
| KR | 20150078191 | A | 7/2015 |
| KR | 101580071 | B1 | 12/2015 |
| KR | 101647620 | B1 | 8/2016 |
| KR | 20160093990 | A | 8/2016 |
| KR | 20170038837 | A | 4/2017 |
| KR | 20180004928 | A | 1/2018 |
| KR | 20190029175 | A | 3/2019 |
| KR | 20190056116 | A | 5/2019 |
| KR | 101988167 | B1 | 6/2019 |
| KR | 101969392 | B1 | 8/2019 |
| KR | 102055279 | B1 | 12/2019 |
| KR | 20200019548 | A | 2/2020 |
| KR | 102088333 | B1 | 3/2020 |
| KR | 20200025290 | A | 3/2020 |
| KR | 20200029180 | A | 3/2020 |
| KR | 102097190 | B1 | 4/2020 |
| KR | 102116664 | B1 | 5/2020 |
| KR | 102116968 | B1 | 5/2020 |
| KR | 20200056233 | A | 5/2020 |
| KR | 102120828 | B1 | 6/2020 |
| KR | 102121586 | B1 | 6/2020 |
| KR | 102142713 | B1 | 8/2020 |
| KR | 102162522 | B1 | 10/2020 |
| KR | 20200119665 | A | 10/2020 |
| KR | 102173553 | B1 | 11/2020 |
| KR | 102180079 | B1 | 11/2020 |
| KR | 102188766 | B1 | 12/2020 |
| KR | 102196793 | B1 | 12/2020 |
| KR | 20210006212 | A | 1/2021 |
| KR | 102224188 | B1 | 3/2021 |
| KR | 102224618 | B1 | 3/2021 |
| KR | 102246049 | B1 | 4/2021 |
| KR | 102246050 | B1 | 4/2021 |
| KR | 102246051 | B1 | 4/2021 |
| KR | 102246052 | B1 | 4/2021 |
| KR | 20210052028 | A | 5/2021 |
| KR | 102264498 | B1 | 6/2021 |
| KR | 102352602 | B1 | 1/2022 |
| KR | 102352603 | B1 | 1/2022 |
| KR | 102352604 | B1 | 1/2022 |
| KR | 20220004639 | A | 1/2022 |
| KR | 102387577 | B1 | 4/2022 |
| KR | 102421437 | B1 | 7/2022 |
| KR | 20220102207 | A | 7/2022 |
| KR | 102427545 | B1 | 8/2022 |
| KR | 102467495 | B1 | 11/2022 |
| KR | 102467496 | B1 | 11/2022 |
| KR | 102469723 | B1 | 11/2022 |
| KR | 102471990 | B1 | 11/2022 |
| KR | 20220145989 | A | 11/2022 |
| KR | 20220156134 | A | 11/2022 |
| KR | 102502744 | B1 | 2/2023 |
| KR | 20230019349 | A | 2/2023 |
| KR | 20230019350 | A | 2/2023 |
| KR | 20230026556 | A | 2/2023 |
| KR | 20230026668 | A | 2/2023 |
| KR | 20230040526 | | 3/2023 |
| KR | 20230050506 | A | 4/2023 |
| KR | 20230056118 | A | 4/2023 |
| KR | 102528503 | B1 | 5/2023 |
| KR | 102531930 | B1 | 5/2023 |
| KR | 102532766 | B1 | 5/2023 |
| KR | 102539190 | B1 | 6/2023 |
| RU | 2014131288 | A | 2/2016 |
| RU | 2607953 | C2 | 1/2017 |
| TW | M474545 | U | 3/2014 |
| TW | I442956 | B | 7/2014 |
| TW | M638437 | U | 3/2023 |
| WO | 1998009687 | A1 | 3/1998 |
| WO | 0149235 | A2 | 7/2001 |
| WO | 0151083 | A2 | 7/2001 |
| WO | 2001050387 | A1 | 7/2001 |
| WO | 2001056465 | A1 | 8/2001 |
| WO | 02062211 | A2 | 8/2002 |
| WO | 02093312 | A2 | 11/2002 |
| WO | 2003043494 | A1 | 5/2003 |
| WO | 2005018453 | A1 | 3/2005 |
| WO | 2005074369 | A2 | 8/2005 |
| WO | 2006004430 | A2 | 1/2006 |
| WO | 2006012694 | A1 | 2/2006 |
| WO | 2007102709 | A1 | 9/2007 |
| WO | 2008114291 | A1 | 9/2008 |
| WO | 2008140780 | A1 | 11/2008 |
| WO | 2009003170 | A1 | 12/2008 |
| WO | 2009008968 | A1 | 1/2009 |
| WO | 2011025322 | A2 | 3/2011 |
| WO | 2012128801 | A1 | 9/2012 |
| WO | 2013002568 | A2 | 1/2013 |
| WO | 2023164292 | A1 | 3/2013 |
| WO | 2013122839 | A1 | 8/2013 |
| WO | 2014011447 | A1 | 1/2014 |
| WO | 2014163976 | A1 | 10/2014 |
| WO | 2015026744 | A1 | 2/2015 |
| WO | 2015065298 | A1 | 5/2015 |
| WO | 2015082555 | A1 | 6/2015 |
| WO | 2016151364 | A1 | 9/2016 |
| WO | 2016154318 | A1 | 9/2016 |
| WO | 2017030781 | A1 | 2/2017 |
| WO | 2017166074 | A1 | 5/2017 |
| WO | 2017091691 | A1 | 6/2017 |
| WO | 2017165238 | A1 | 9/2017 |
| WO | 2018027080 | A1 | 2/2018 |
| WO | 2018081795 | A1 | 5/2018 |
| WO | 2018171853 | A1 | 9/2018 |
| WO | 2019022706 | A1 | 1/2019 |
| WO | 2019106003 | A1 | 6/2019 |
| WO | 2019143940 | A1 | 7/2019 |
| WO | 2020014710 | A2 | 1/2020 |
| WO | 2020075190 | A1 | 4/2020 |
| WO | 2020130979 | A1 | 6/2020 |
| WO | 2020149815 | A2 | 7/2020 |
| WO | 2020229705 | A1 | 11/2020 |
| WO | 2020245727 | A1 | 12/2020 |
| WO | 2020249855 | A1 | 12/2020 |
| WO | 2020252599 | A1 | 12/2020 |
| WO | 2020256577 | A1 | 12/2020 |
| WO | 2021021447 | A1 | 2/2021 |
| WO | 2021022003 | A1 | 2/2021 |
| WO | 2021038980 | A1 | 3/2021 |
| WO | 2021055427 | A1 | 3/2021 |
| WO | 2021061061 | A1 | 4/2021 |
| WO | 2021090267 | A1 | 5/2021 |
| WO | 2021138620 | A1 | 7/2021 |
| WO | 2021216881 | A1 | 10/2021 |
| WO | 2021236961 | A1 | 11/2021 |
| WO | 2022047006 | A1 | 3/2022 |
| WO | 2022092493 | A1 | 5/2022 |
| WO | 2022092494 | A1 | 5/2022 |
| WO | 2022212883 | A1 | 10/2022 |
| WO | 2022212921 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |
| WO | 2024013267 | A1 | 1/2024 |
| WO | 2024107807 | A1 | 5/2024 |

(56)            References Cited

OTHER PUBLICATIONS

Acampora, Giovanni et al. A Survey on Ambient Intelligence in Healthcare. Proceedings of the IEEE vol. 101, Issue 12, 2013. (Year: 2013).*

HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.

International Searching Authority, International Preliminary Report on Patentability of International Application No. PCT/US2017/50895, Date of Mailing Dec. 11, 2018, 52 pages.

International Searching Authority, Search Report and Written Opinion for International Application No. PCT/US2017/50895, Date of Mailing Jan. 12, 2018, 6 pages.

International Searching Authority, Search Report and Written Opinion for International Application No. PCT/US2020/021876, Date of Mailing May 28, 2020, 8 pages.

International Searching Authority, Search Report and Written Opinion for International Application No. PCT/US2020/051008, Date of Mailing Dec. 10, 2020, 9 pages.

International Searching Authority, Search Report and Written Opinion for International Application No. PCT/US2020/056661, Date of Mailing Feb. 12, 2021, 12 pages.

International Searching Authority, Search Report and Written Opinion for International Application No. PCT/US2021/032807, Date of Mailing Sep. 6, 2021, 11 pages.

Matrix, R3xm Recumbent Cycle, retrieved on Aug. 4, 2020, 7 pages, https://www.matrixfitness.com/en/cardio/cycles/r3xm-recumbent.

ROM3 Rehab, ROM3 Rehab System, Apr. 20, 2015, retrieved on Aug. 31, 2018, 12 pages, https://vimeo.com/125438463.

Jeong et al., "Remotely controlled biking is associated with improved adherence to prescribed cycling speed," Technology and Health Care 23, 2015, 7 pages.

Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.

Blasiak et al., "Curate.AI: Optimizing Personalized Medicine with Artificial Intelligence,"Slas Technology: Translating Life Sciences Innovation, 2020, 11 pages.

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.

Abedtash, "An Interoperable Electronic Medical Record-Based Platform for Personalized Predictive Analytics", ProQuest LLC, Jul. 2017, 185 pages.

Amiya et al., "Is Exercise Training Appropriate for Patients With Advanced Heart Failure Receiving Continuous Inotropic Infusion? A Review," 2018, pp. 1-9, vol. 12, Japan.

Chu Hin Yee, "Physical Activity, Sedentary Behaviour and Health: From Measurements to Recommendations," 2018, 255 pages.

Gerbild et al., "Physical Activity to Improve Erectile Dysfunction: A Systematic Review of Intervention Studies," Sexual Medicine, 2018, 15 pages.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

Lima de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities for Artificial Intelligence to Transform How Care Is Delivered," Nov. 2019, American Hospital Association, pp. 1-12.

Ahmed et al., "Artificial Intelligence With Multi-Functional Machine Learning Platform Development for Better Healthcare and Precision Medicine," Database (Oxford), 2020, pp. 1-35, vol. 2020.

Davenport et al., "The Potential for Artificial Intelligence in Healthcare," Future Healthcare Journal, 2019, pp. 94-98, vol. 6, No. 2.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.

Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.

Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.

Ahmed et al., "Artificial intelligence with multi-functional machine learning platform development for better healthcare and precision medicine," Database, 2020, pp. 1-35.

Davenport et al., "The potential for artificial intelligence in healthcare," Digital Technology, Future Healthcare Journal, 2019, pp. 1-5, vol. 6, No. 2.

Website for "OxeFit XS1", pp. 1-3, retrieved on Sep. 9, 2022 from https://www.oxefit.com/xs1.

Website for "Preva Mobile", pp. 1-6, retrieved on Sep. 9, 2022 from https://www.precor.com/en-us/resources/introducing-preva-mobile.

Website for "J-Bike", pp. 1-3, retrieved on Sep. 9, 2022 from https://www.magneticdays.com/en/cycling-for-physical-rehabilitation.

Website for "Excy", pp. 1-12, retrieved on Sep. 9, 2022 from https://excy.com/portable-exercise-rehabilitation-excy-xcs-pro/.

Website for "OxeFit XP1", p. 1, retrieved on Sep. 9, 2022 from https://www.oxefit.com/xp1.

Chrif et al., "Control design for a lower-limb paediatric therapy device using linear motor technology," Article, 2017, pp. 119-127, Science Direct, Switzerland.

(56) References Cited

OTHER PUBLICATIONS

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the Par-•Q+ and ePARmed-•X+ Validation of the PAR-•Q+ and ePARmed••X+," Health & Fitness Journal of Canada, 2011, 9 pages, vol. 4, No. 2.

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.

Androutsou et al., "A Smartphone Application Designed to Engage the Elderly in Home-Based Rehabilitation," Frontiers in Digital Health, Sep. 2020, vol. 2, Article 15, 13 pages.

Silva et al., "SapoFitness: A mobile health application for dietary evaluation," 2011 IEEE 13th International Conference on U e-Health Networking, Applications and Services, Columbia, MO, USA, 2011, 6 pages.

Wang et al., "Interactive wearable systems for upper body rehabilitation: a systematic review," Journal of NeuroEngineering and Rehabilitation, 2017, 21 pages.

Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.

Nijjar et al., "Randomized Trial of Mindfulness-Based Stress Reduction in Cardiac Patients Eligible for Cardiac Rehabilitation," Scientific Reports, 2019, 12 pages.

Lara et al., "Human-Robot Sensor Interface for Cardiac Rehabilitation," IEEE International Conference on Rehabilitation Robotics, Jul. 2017, 8 pages.

Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

You et al., "Including Blood Vasculature into a Game-Theoretic Model of Cancer Dynamics," Games 2019, 10, 13, 22 pages.

Jeong et al., "Computer-assisted upper extremity training using interactive biking exercise (iBikE) platform," Sep. 2012, 34th Annual International Conference of the IEEE EMBS, 5 pages.

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Davenport et al., "The Potential for Artificial Intelligence in Healthcare", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pages 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Jeong et al., "Computer-assisted upper extremity training using interactive biking exercise (iBikE) platform," Sep. 2012, pp. 1-5, 34th Annual International Conference of the IEEE EMBS.

Malloy, Online Article "Al-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12: 1-19. Springer Nature B.V. (Dec 2017) (Year: 2017).

Fuller, Carole G.; Diagnosis and treatment considerations with comorbid developmentally disabled populations; Journal of Clinical Psychology 54.1: 1-10. John VWey and Sons Inc. (Jan 1998) (Year: 1998).

cG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC20132262913. (Year: 2013).

H. Demirkan, "A Smart Healthcare Systems Framework," in IT Professional, vol. 15, No. 5, pp. 38-45, Sep.-Oct. 2013, doi: 10.1109/MITP.2013.35. (Year: 2013).

W. Rashwan, J. Fowler and A. Arisha, "A Multi-Method Scheduling Framework for Medical Staff," 2018 Winter Simulation Conference (WSC), Gothenburg, Sweden, 2018, pp. 1464-1475, doi: 10.1109/WSC.2018.8632247. (Year: 2018).

Marios et al., "The effect of tele-monitoring on exercise training adherence, functional capacity, quality of life and glycemic control in patients with type II diabetes," Journal of Sports Science and Medicine, Mar. 2012, vol. 11, 6 pages.

Shen et al, "Intelligent inverse treatment planning via deep reinforcement learning, a proof-of-principle study in high dose-rate brachytherapy for cervical cancer," pp. 1-17, May 29, 2019, Phys. Med. Biol. vol. 64, No. 115013.

Fraass et al, "The impact of treatment complexity and computer-control delivery technology on treatment delivery errors," pp. 651-659, Oct. 1, 1998, International Journal of Radiation Oncology Biology Physics, vol. 42, Issue 3, https://doi.org/:10.1016/s0360-3016(98)00244-2. PMID: 9806527.

Marchal-Crespo et al, "Review of control strategies for robotic movement training after neurologic injury," pp. 1-15, Jun. 16, 2009, Journal of NeuroEngineering and Rehabilitation, vol. 6, No. 20, https://doi.org/10.1186/1743-0003-6-20.

Karboub et al, "A Machine Learning Based Discharge Prediction of Cardiovascular Diseases Patients in Intensive Care Units.," pp. 1-23, May 24, 2022, Healthcare (Basel, Switzerland) MDPI, vol. 10(6), No. 966, https://doi.org/10.3390/healthcare10060966.

Chrif et al, "Control design for a lower-limb paediatric therapy device using linear motor technology," pp. 119-127, Jun. 9, 2017, Biomedical Usignal Processing and Control, vol. 38, https://www.sciencedirect.com/science/article/pii/S1746809417301027.

(56) References Cited

OTHER PUBLICATIONS

International Preliminary Report on Patentability of International Application No. PCT/2024/022550, Date of Mailing Sep. 20, 2025, 7 pages.

Capecci et al. 2016, "Physical rehabilitation exercises assessment based on Hidden Semi-Marlkov Model by Kinect v2," 2016 IEEE-EMBS International Conference on Biomedical and Health Informatics (BHI), Las Vegas, NV, USA, 2016, pp. 256-259, doi: 10.1109/BH 1.2016. 7 455883.

Cespedes et al. 2020, "Social Human-Robot Interaction for Gait Rehabilitation," in IEEE Transactions on Neural Systems and Rehabilitation Engineering, vol. 28, No. 6, pp. 1299-1307, Jun. 2020, doi: 10.1109/TNSRE.2020.2987428.

Jamil, Faisal, et al. "Towards secure fitness framework based on IoT-enabled blockchain network integrated with machine learning algorithms." Sensors 21.5 (2021): 1640. (Year: 2021).

* cited by examiner

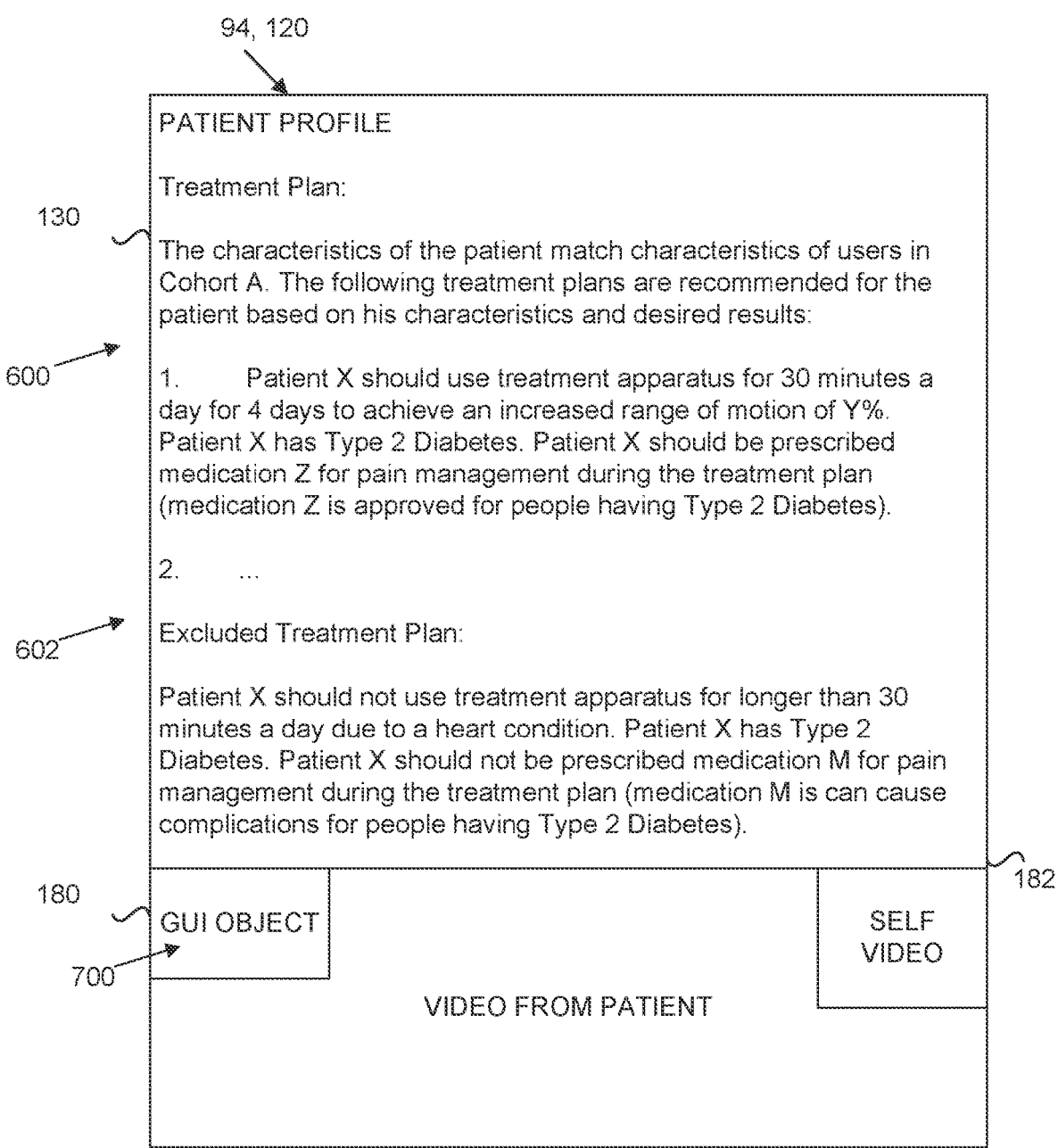

94, 120

130

600

602

180

700

182

PATIENT PROFILE

Treatment Plan:

The characteristics of the patient match characteristics of users in Cohort A. The following treatment plans are recommended for the patient based on his characteristics and desired results:

1.      Patient X should use treatment apparatus for 30 minutes a day for 4 days to achieve an increased range of motion of Y%. Patient X has Type 2 Diabetes. Patient X should be prescribed medication Z for pain management during the treatment plan (medication Z is approved for people having Type 2 Diabetes).

2.      ...

Excluded Treatment Plan:

Patient X should not use treatment apparatus for longer than 30 minutes a day due to a heart condition. Patient X has Type 2 Diabetes. Patient X should not be prescribed medication M for pain management during the treatment plan (medication M is can cause complications for people having Type 2 Diabetes).

GUI OBJECT                          SELF
                                    VIDEO

VIDEO FROM PATIENT

FIG. 7

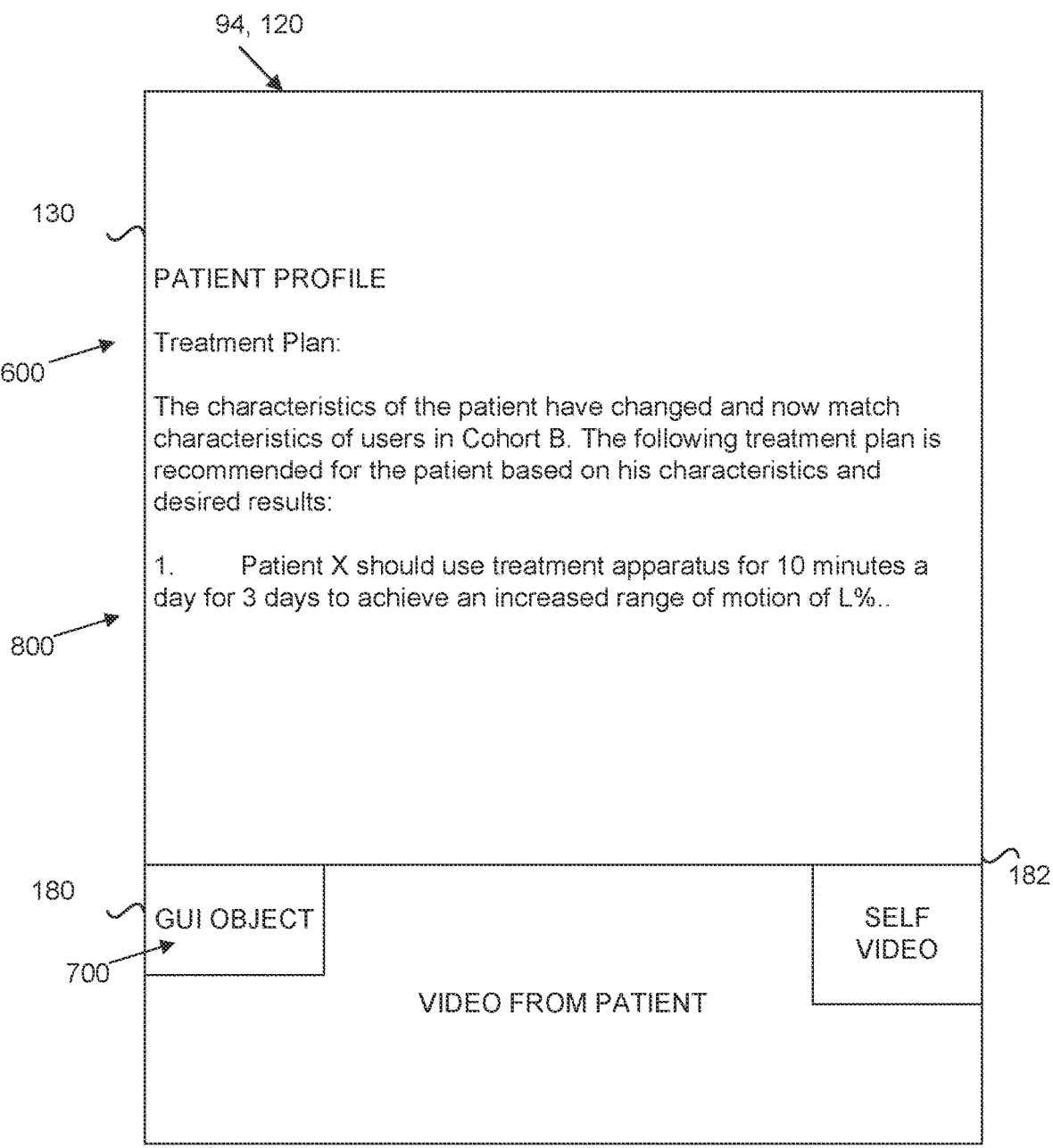

94, 120

130

600

800

PATIENT PROFILE

Treatment Plan:

The characteristics of the patient have changed and now match characteristics of users in Cohort B. The following treatment plan is recommended for the patient based on his characteristics and desired results:

1.     Patient X should use treatment apparatus for 10 minutes a day for 3 days to achieve an increased range of motion of L%..

180

700

GUI OBJECT

VIDEO FROM PATIENT

SELF VIDEO

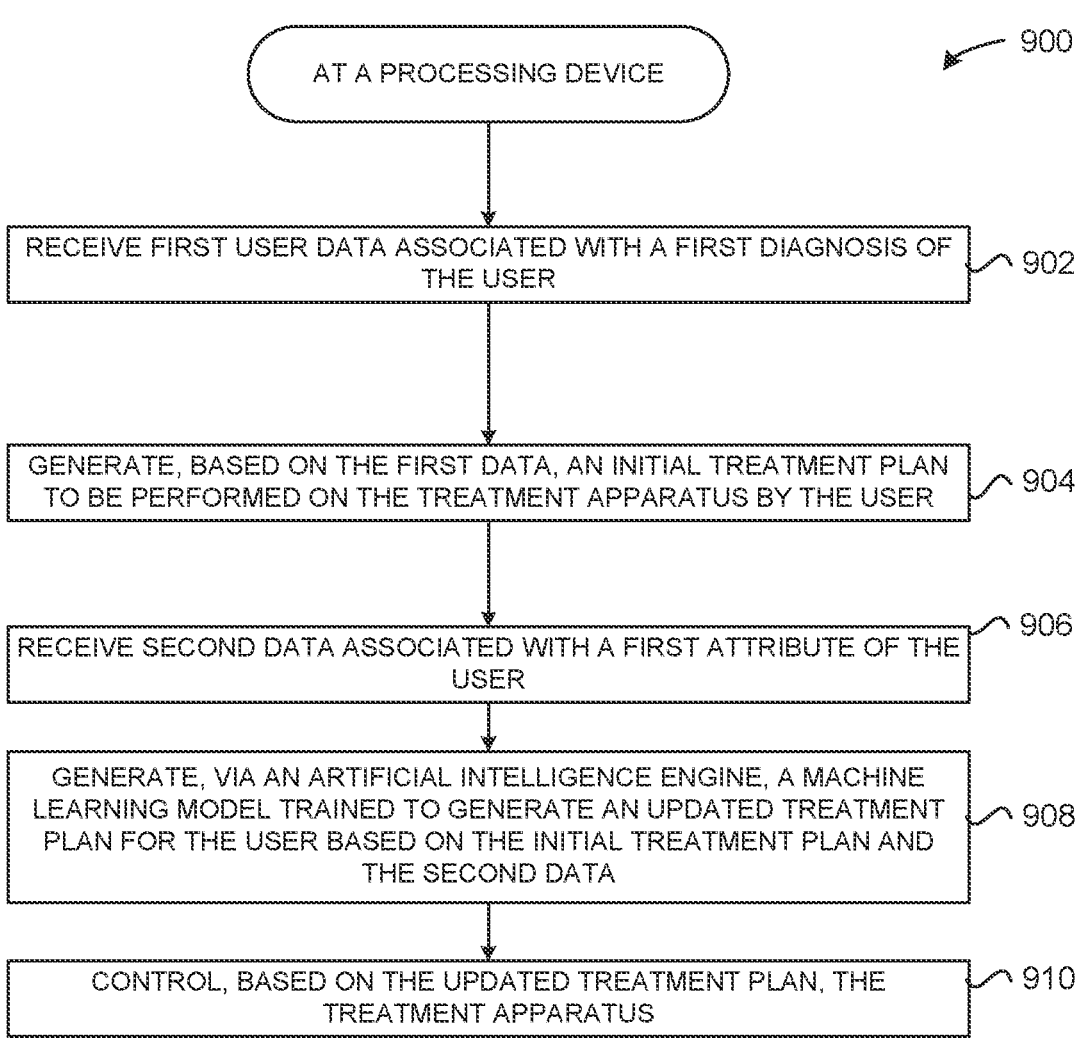

900

AT A PROCESSING DEVICE

RECEIVE FIRST USER DATA ASSOCIATED WITH A FIRST DIAGNOSIS OF THE USER ⟩ 902

GENERATE, BASED ON THE FIRST DATA, AN INITIAL TREATMENT PLAN TO BE PERFORMED ON THE TREATMENT APPARATUS BY THE USER ⟩ 904

RECEIVE SECOND DATA ASSOCIATED WITH A FIRST ATTRIBUTE OF THE USER ⟩ 906

GENERATE, VIA AN ARTIFICIAL INTELLIGENCE ENGINE, A MACHINE LEARNING MODEL TRAINED TO GENERATE AN UPDATED TREATMENT PLAN FOR THE USER BASED ON THE INITIAL TREATMENT PLAN AND THE SECOND DATA ⟩ 908

CONTROL, BASED ON THE UPDATED TREATMENT PLAN, THE TREATMENT APPARATUS ⟩ 910

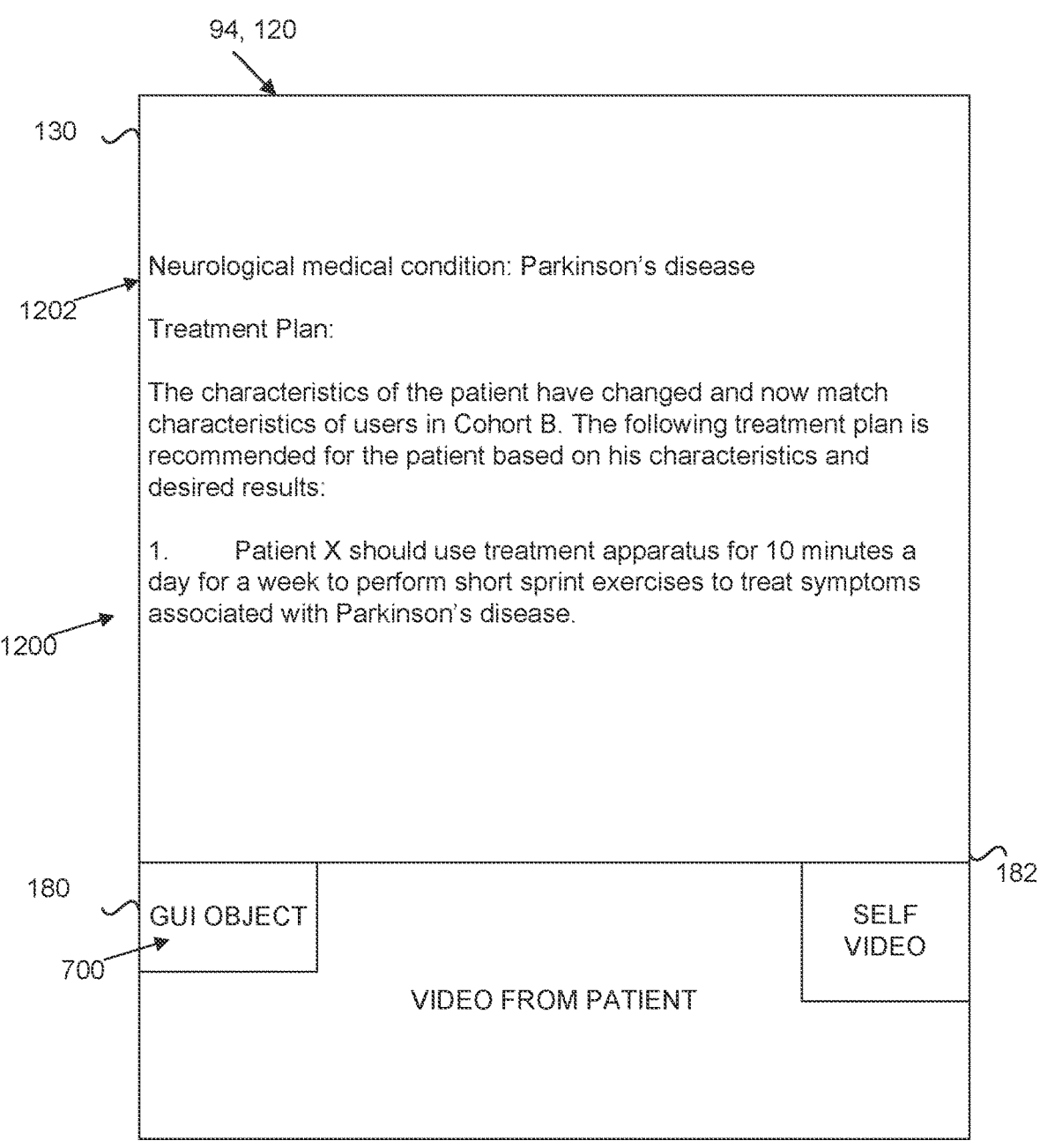

Neurological medical condition: Parkinson's disease

Treatment Plan:

The characteristics of the patient have changed and now match characteristics of users in Cohort B. The following treatment plan is recommended for the patient based on his characteristics and desired results:

1.      Patient X should use treatment apparatus for 10 minutes a day for a week to perform short sprint exercises to treat symptoms associated with Parkinson's disease.

180

700

GUI OBJECT

VIDEO FROM PATIENT

SELF VIDEO

SYSTEM AND METHOD FOR USING AN ARTIFICIAL INTELLIGENCE ENGINE TO OPTIMIZE A TREATMENT PLAN

CROSS-REFERENCES TO RELATED APPLICATIONS

This application is a continuation-in-part of U.S. patent application Ser. No. 17/736,891, filed May 4, 2022, titled "Systems and Methods for Using Artificial Intelligence to Implement a Cardio Protocol via Relay-Based System," which is a continuation-in-part of U.S. patent application Ser. No. 17/379,542, filed Jul. 19, 2021, now issued U.S. Pat. No. 11,328,807, titled "System and Method for Using Artificial Intelligence in Telemedicine-Enabled Hardware to Optimize Rehabilitative Routines Capable of Enabling Remote Rehabilitative Compliance," which is a continuation of U.S. patent application Ser. No. 17/146,705, filed Jan. 12, 2021, titled "System and Method for Using Artificial Intelligence in Telemedicine-Enabled Hardware to Optimize Rehabilitative Routines Capable of Enabling Remote Rehabilitative Compliance," which is a continuation-in-part of U.S. patent application Ser. No. 17/021,895, filed Sep. 15, 2020, now issued U.S. Pat. No. 11,071,597, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. The application U.S. patent application Ser. No. 17/146,705 also claims priority to and the benefit of U.S. Provisional Patent Application Ser. No. 63/113,484, filed Nov. 13, 2020, titled "System and Method for Use of Artificial Intelligence in Telemedicine-Enabled Hardware to Optimize Rehabilitative Routines for Enabling Remote Rehabilitative Compliance," the entire disclosures of which are hereby incorporated by reference for all purposes.

This application also claims the benefit of U.S. Patent Application Ser. No. 63/238,957, filed Aug. 31, 2021, titled "System and Method for Using an Artificial Intelligence Engine to Optimize a Treatment Plan," the entire disclosure of which is hereby incorporated by reference for all purposes.

BACKGROUND

Remote medical assistance, or telemedicine, may aid a patient in performing various aspects of a rehabilitation regimen for a body part. The patient may use a patient interface in communication with an assistant interface for receiving the remote medical assistance via audio, visual, and/or audiovisual communications.

SUMMARY

An aspect of the disclosed embodiments includes a method for updating a treatment plan. The treatment plan may be associated with a user using a treatment apparatus to perform the treatment plan. The method may comprise receiving first data associated with a first diagnosis of the user. The method may comprise generating, based on the first data, an initial treatment plan to be performed on the treatment apparatus by the user. The method may comprise receiving second data associated with a first attribute of the user. The method may also comprise generating, via an artificial intelligence engine, a machine learning model trained to generate an updated treatment plan that is based on the initial treatment plan and the second data.

Another aspect of the disclosed embodiments comprises a system for updating a treatment plan associated with a user using a treatment apparatus to perform the treatment plan. The system may comprise a processing device. The system may also comprise a memory including instructions that, when executed by the processing device, cause the processing device to receive first data associated with a first diagnosis of the user. The instructions may cause the processing device to generate, based on the first data, an initial treatment plan to be performed on the treatment apparatus by the user. The instructions may cause the processing device to receive second data associated with a first attribute of the user. The instructions may also cause the processing device to generate, via an artificial intelligence engine, a machine learning model trained to generate an updated treatment plan for the user, wherein the updated treatment plan is based on the initial treatment plan and the second data.

Another aspect of the disclosed embodiments comprises a tangible, non-transitory machine-readable medium storing instructions that, when executed, cause a processing device to perform any of the operations, steps, functions, and/or methods disclosed herein.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 7 generally illustrates an embodiment of an overview display of the assistant interface presenting recommended treatment plans and excluded treatment plans in real-time during a telemedicine session according to the principles of the present disclosure.

FIG. 8 generally illustrates an embodiment of the overview display of the assistant interface presenting, in real-time during a telemedicine session, recommended treatment plans that have changed as a result of patient data changing according to the principles of the present disclosure.

FIG. 9 is a flow diagram generally illustrating a method for updating a treatment plan according to the principles of the present disclosure.

FIG. 12 generally illustrates an embodiment of the overview display of the assistant interface presenting, in real-time during a telemedicine session, an updated treatment plan based on a diagnosed medical condition of the user according to the principles of the present disclosure.

NOTATION AND NOMENCLATURE

Figure 1:
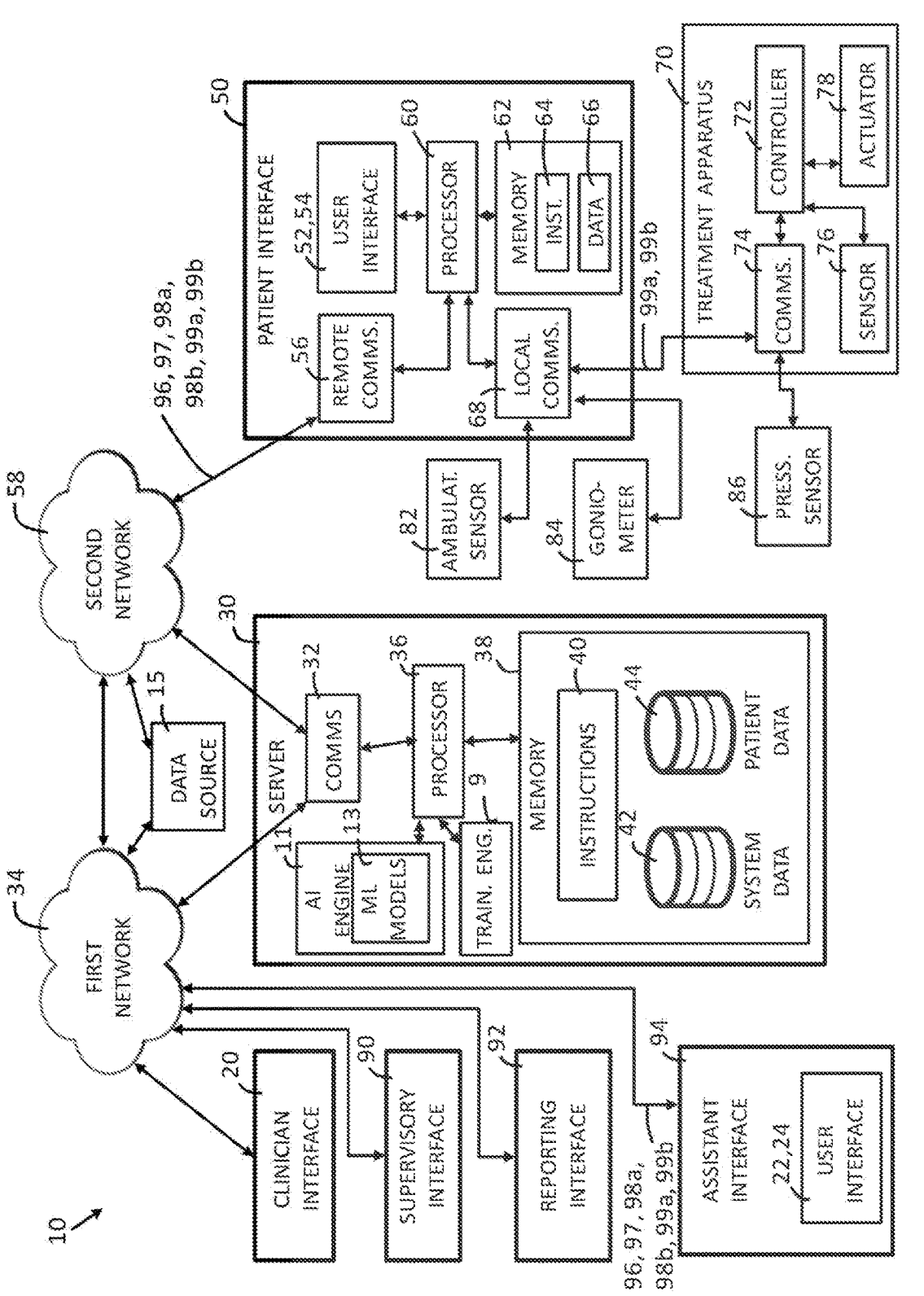
FIG. 1 generally illustrates a block diagram of an embodiment of a computer-implemented system for managing a treatment plan according to the principles of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The terms telemedicine, telehealth, telemed, teletherapeutic, remote medicine, etc. may be used interchangeably herein. The term "condition" may be used to refer to a disease or other attribute of the user.

As used herein, the term healthcare professional may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare professional" may be a human being, a robot, a virtual assistant, a virtual assistant in virtual and/or augmented reality, or an artificially intelligent entity, such entity including a software program, integrated software and hardware, or hardware alone.

As used herein, the terms treatment apparatus, exercise apparatus, exercise device, treatment device, electromechanical machine, electromechanical device, workout device, workout apparatus, rehabilitation apparatus, rehabilitation device, rehabilitation machine, prehabilitatoin apparatus, prehabilitation device, and/or prehabilitation machine may be used interchangeably herein.

As used herein, the term "jerk" may refer to moving the portion of the exercise apparatus as quickly as possible from an initial position to a second stationary position.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining a treatment plan for a patient having certain characteristics (e.g., vital-sign or other measurements; performance; demographic; geographic; diagnostic; measurement- or test-based; medically historic; behavioral historic; cognitive; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, a range of motion achieved on the treatment apparatus, a speed or a velocity of a moving portion of the treatment apparatus, an indication of a plurality of pain levels using the treatment apparatus, or some combination thereof. The measurement information may include, e.g., a vital sign, a respiration rate, a heartrate, a temperature, a blood pressure, or some combination thereof. It may be desirable to process the characteristics of a multitude of patients, the treatment plans performed for those patients, and the results of the treatment plans for those patients.

Further, another technical problem may involve distally treating, via a computing device during a telemedicine or telehealth session, a patient from a location different than a location at which the patient is located. An additional technical problem is controlling or enabling the control of, from the different location, a treatment apparatus used by the patient at the location at which the patient is located. Oftentimes, when a patient undergoes rehabilitative surgery (e.g., knee surgery), a physical therapist or other medical professional may prescribe a treatment apparatus to the patient to use to perform a treatment protocol at their residence or any mobile location or temporary domicile. A medical professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

When the healthcare professional is located in a different location from the patient and the treatment apparatus, it may be technically challenging for the healthcare professional to monitor the patient's actual progress (as opposed to relying on the patient's word about their progress) using the treatment apparatus, modify the treatment plan according to the patient's progress, adapt the treatment apparatus to the personal characteristics of the patient as the patient performs the treatment plan, and the like.

Additionally, or alternatively, the two or more healthcare professionals may treat the patient (e.g., for the same condition, different conditions, related conditions, and the like). For example, an orthopedic surgeon, a physical therapist, and/or one or more other healthcare professionals may cooperatively or independent treat or be responsible for treatment of the patient for the same condition or a related condition. Such healthcare professionals may be located remotely from the patient and/or one another. Accordingly, systems and methods, such as those described herein, that coordinate schedules of the two or more healthcare professionals to provide treatment to the patient via a telemedicine session, may be desirable.

Accordingly, embodiments of the present disclosure pertain to using artificial intelligence and/or machine learning to assign patients to cohorts and to dynamically control a treatment apparatus based on the assignment during an adaptive telemedical session. In some embodiments, numerous treatment apparatuses may be provided to patients. The treatment apparatuses may be used by the patients to perform treatment plans in their residences, at a gym, at a rehabilitative center, at a hospital, or any suitable location, including permanent or temporary domiciles.

In some embodiments, the systems and methods described herein may be configured for generating treatment plans for users that are diagnosed with one or more medical conditions. In some embodiments, in particular, the diagnosed medical conditions may be related to neurological conditions and/or neurological conditions. Each physiological condition and/or neurological condition may be associated with one or more symptoms that are treatable by performing various exercises. There may be combinatorial effects that are not conventionally accounted for in rehabilitation regimens when a user has more than one medical condition. Accordingly, in some embodiments, using artificial intelligence and machine learning, a treatment plan may be generated that optimizes the exercises performed to treat the symptoms related to each medical condition diagnosed for a user.

In some embodiments, an initial treatment plan may be generated for a user based on a first diagnosis of the user. The first diagnosis may be determined via an electronic medical record system that uses one or more diagnostic codes (e.g., International Classification of Diseases (ICD) codes, Diagnosis-Related Group (DRG) codes, etc.) to indicate the diagnosis of the first user. The codes may be related to neurological conditions, such as degeneration, dysfunction, disorder, trauma, developmental delay, and the like. The codes may be related to other physiological and/or anatomical conditions, such as tears, breaks, ruptures, sprains, swells, surgeries, procedures, diseases, immunomodulatory conditions, genetic or epigenetic conditions, etc. One or more machine learning models may be trained on a corpus of training data to receive one or more diagnoses of the user and to output a treatment plan that includes one or more exercises using a treatment apparatus. The treatment plan may be optimized to provide a desired goal for the one or more diagnoses.

To that end, different diagnoses may be associated with different goals for the user. For example, the goal for a user diagnosed with Alzheimer's disease may include staving off progression of the disease to a greatest extent possible, and the treatment plan may include exercises that are expected (based on clinical research) to limit the progression of the disease. In another example, a user may be recovering from a neurologically traumatic accident where the goal is to increase and/or potentiate neuroplasticity. Accordingly, the goal for the neurological trauma may include regenerating and/or developing new synaptic pathways. In such cases, the treatment plan for the neurological trauma may include exercises that are expected (based on clinical research) to regenerate and/or develop new synaptic pathways. In another example, a user may be recovering from knee surgery, and a goal may include increasing a range of motion of movement of the knee. Accordingly, the treatment plan may include exercises that gradually increase a range of motion of the user's knee while the user is pedaling. The machine learning models may be trained to generate various treatment plans based on the various diagnoses, such that each diagnosis may be treated in an optimal manner.

As the user performs a generated treatment plan, various data associated with the user may be received from one or more sensors, a user interface, an electronic medical record system, other computing devices, and the like. The data may include one or more measurements of a vital sign of the user, a respiration rate of the user, a heartrate of the user, a heart rhythm of a user, an oxygen saturation level of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the treatment apparatus, an amount of force exerted by the user on a portion of the treatment apparatus, a range of motion achieved by the user on the treatment apparatus, a speed or velocity measurement of a moving portion of the treatment apparatus, a pressure exerted by the user on a portion of the exercise apparatus, an acceleration measurement of a moving portion of the exercise apparatus, a jerk of a portion of the exercise apparatus, a torque level induced by the user on a portion of the exercise apparatus, an indication of a plurality of pain levels experienced by the user when using the treatment apparatus, or some combination thereof.

The data received may be transmitted to a computing device of a healthcare professional and/or an artificial intelligence engine. Based on the received data, a second diagnosis may be determined in real-time or near real-time. The second diagnosis may include a neurological condition that affects at least one function of the user. Examples of such functions which may be included comprise: a somatic function, a psychological function, a behavioral function, a dexterity function, a cerebral function, a physiological function, an anatomical function, a cardiac function, a neurological function, an endocrinological function, a cognitive function, or some combination thereof. One or more machine learning models may be trained to generate, based on the initial treatment plan, the received data, and/or the second diagnosis, an updated treatment plan for the user. The updated treatment plan may include one or more exercises, operating parameters of the treatment apparatus, or both, wherein any of the foregoing are associated with achieving one or more goals for the first diagnosis and/or the second diagnosis. Accordingly, some embodiments of the present disclosure may enable the generation of enhanced treatment plans that may produce desired results (goals) for one or more complex physiological and/or neurological conditions of a user. For example, by using the exercise apparatus to perform one or more exercises associated with the goals of the medical conditions, the enhanced treatment plans may enable simultaneous or concurrent recovering from neurological trauma, reducing a neurological degradation rate, increasing a range of motion of a joint, reducing blood pressure, etc. In some embodiments, the server may be configured to control in real-time or near real-time, based on the updated treatment plan, the treatment apparatus.

In some embodiments, the treatment apparatuses may be communicatively coupled to a server. Characteristics of the patients, including the treatment data may be collected before, during, and/or after the patients perform the treatment plans. For example, any or each of personal information, the performance information, and the measurement information may be collected before, during, and/or after the person performs the treatment plans. The results (e.g., improved performance or decreased performance) of performing each exercise may be collected from the treatment apparatus throughout the treatment plan and after the treatment plan is performed. The parameters, settings, configurations, etc. (e.g., position of pedal, amount of resistance, etc.) of the treatment apparatus may be collected before, during, and/or after the treatment plan is performed.

Each characteristic of the patient, each result, and each parameter, setting, configuration, etc. may be timestamped and may be correlated with a particular step in the treatment plan. Such a technique may enable determining which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment apparatuses and/or any suitable computing device (e.g., computing devices where personal information is entered, such as a clinician interface or patient interface) over time as the patients use the treatment apparatuses to perform the various treatment plans. The data that may be collected may include the characteristics of the patients, the treatment plans performed by the patients, and the results of the treatment plans.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment apparatus for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment apparatus while the new patient uses the treatment apparatus to perform the treatment plan.

As may be appreciated, the characteristics of the new patient may change as the new patient uses the treatment apparatus to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion. A different treatment plan may be selected for the new patient, and the treatment apparatus may be controlled, distally and based on the different treatment plan, the treatment apparatus while the new patient uses the treatment apparatus to perform the treatment plan. Such techniques may provide the technical solution of distally controlling a treatment apparatus. Further, the techniques may lead to faster recovery times and/or better results for the patients because the treatment plan that most accurately fits their characteristics is selected and implemented, in real-time, at any given moment. "Real-time" may also refer to near real-time, which may be less than 10 seconds. As described herein, the term "results" may refer to medical results or medical outcomes. Results and outcomes may refer to responses to medical actions.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may also be trained to output treatment plans that are not optimal or sub-optimal or even inappropriate (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient.

In some embodiments, the treatment plans and/or excluded treatment plans may be presented, during a telemedicine or telehealth session, to a medical professional. The medical professional may select a particular treatment plan for the patient to cause that treatment plan to be transmitted to the patient and/or to control, based on the treatment plan, the treatment apparatus. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment apparatus. In such cases, the recommended treatment plans and/or excluded treatment plans may be presented simultaneously with a video of the patient in real-time or near real-time during a telemedicine or telehealth session on a user interface of a computing device of a medical professional. The video may also be accompanied by audio, text and other multimedia information. Real-time may refer to less than or equal to 2 seconds. Near real-time may refer to any interaction of a sufficiently short time to enable two individuals to engage in a dialogue via such user interface, and will generally be less than 10 seconds but greater than 2 seconds.

Presenting the treatment plans generated by the artificial intelligence engine concurrently with a presentation of the patient video may provide an enhanced user interface because the medical professional may continue to visually and/or otherwise communicate with the patient while also reviewing the treatment plans on the same user interface. The enhanced user interface may improve the medical professional's experience using the computing device and may encourage the medical professional to reuse the user interface. Such a technique may also reduce computing resources (e.g., processing, memory, network) because the medical professional does not have to switch to another user interface screen to enter a query for a treatment plan to recommend based on the characteristics of the patient. The artificial intelligence engine provides, dynamically on the fly, the treatment plans and excluded treatment plans.

In some embodiments, the treatment apparatus may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a medical professional may adapt, remotely during a telemedicine session, the treatment apparatus to the needs of the patient by causing a control instruction to be transmitted from a server to treatment apparatus. Such adaptive nature may improve the results of recovery for a patient, furthering the goals of personalized medicine, and enabling personalization of the treatment plan on a per-individual basis.

A technical problem may occur which relates to the information pertaining to the patient's medical condition being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). That is, some sources used by various healthcare professionals may be installed on their local computing devices and may use proprietary formats. Accordingly, some embodiments of the present disclosure may use an API to obtain, via interfaces exposed by APIs used by the sources, the formats used by the sources. In some embodiments, when information is received from the sources, the API may map, translate and/or convert the format used by the sources to a standardized format used by the artificial intelligence engine. Further, the information mapped, translated and/or converted to the standardized format used by the artificial intelligence engine may be stored in a database accessed by the artificial intelligence engine when performing any of the techniques disclosed herein. Using the information mapped, translated and/or converted to a standardized format may enable the more accurate determination of the procedures to perform for the patient and/or a billing sequence.

To that end, the standardized information may enable the generation of treatment plans and/or billing sequences having a particular format configured to be processed by various applications (e.g., telehealth). For example, applications, such as telehealth applications, may be executing on various computing devices of medical professionals and/or patients. The applications (e.g., standalone or web-based) may be provided by a server and may be configured to process data according to a format in which the treatment plans are implemented. Accordingly, the disclosed embodiments may provide a technical solution by (i) receiving, from various sources (e.g., EMR systems), information in non-standardized and/or different formats; (ii) standardizing the information; and (iii) generating, based on the standardized information, treatment plans having standardized formats capable of being processed by applications (e.g., telehealth applications) executing on computing devices of medical professional and/or patients.

FIG. 1 generally illustrates a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store (e.g. write to an associated memory) and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

Additionally or alternatively, the characteristics (e.g., personal, performance, measurement, etc.) of the people, the treatment plans followed by the people, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment apparatuses and/or computing devices and/or digital storage media over time and stored in the data store 44. The characteristic data, treatment plan data, and results data may be correlated in the patient-cohort databases in the patient data store 44. The characteristics of the people may include personal information, performance information, and/or measurement information.

In addition to the historical information about other people stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another person in a particular cohort (e.g., cohort A) and the patient may be assigned to that cohort.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their characteristics, select treatment plans using real-time and historical data correlations involving patient cohort-equivalents, and control a treatment apparatus 70, among other things. The machine learning models 13 may be trained to generate, based on data associated with a diagnosis of users, initial treatment plans to be performed on the treatment apparatus 70 by the users. For example, the machine learning models 13 may be trained to provide a visual stimulus, audio stimulus, or haptic stimulus.

The machine learning models 13 may also be configured, for example, to cause a user interface to inform (e.g., via a display, a generated audio signal, and the like) the user of a goal for the day, where the goal is dependent upon the generated treatment plan. For example, the machine learning models may be configured to receive a measurement of a vital sign of the user, a respiration rate of the user, a heartrate of the user, a heart rhythm of a user, an oxygen saturation level of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the treatment apparatus, an amount of force exerted on a portion of the treatment apparatus, a range of motion achieved on the treatment apparatus, a speed measurement of a moving portion of the treatment apparatus, a pressure exerted on a portion of the exercise apparatus, an acceleration measurement of a moving portion of the exercise apparatus, a jerk of a portion of the exercise apparatus, a torque level of a portion of the exercise apparatus, and an indication of a plurality of pain levels experienced by the user when using the treatment apparatus. The measurement may be received as sensor data or, in some embodiments, as input received from a computing device. In some embodiments, the measurements that the machine learning models 13 are trained to monitor may be related to one or more underlying condition or to one or more attributes of the user. In other embodiments, the measurements that the machine learning models 13 are trained to monitor may be related to one or more underlying conditions of the user.

The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other suitable computing device, or a combination thereof. The training engine 9 may be cloud-based or a real-time software platform, and it may include privacy software or protocols, and/or security software or protocols.

To train the one or more machine learning models 13, the training engine 9 may use a training data set of a corpus of the characteristics (e.g., medical diagnoses, attributes, a measurement of a vital sign of the user, a respiration rate of the user, a heartrate of the user, a heart rhythm of a user, an oxygen saturation level of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the treatment apparatus, an amount of force exerted on a portion of the treatment apparatus, a range of motion achieved on the treatment apparatus, a speed measurement of a moving portion of the treatment apparatus, a pressure exerted on a portion of the exercise apparatus, an acceleration measurement of a moving portion of the exercise apparatus, a jerk of a portion of the exercise apparatus, a torque level of a portion of the exercise apparatus, an indication of a plurality of pain levels experienced by the user when using the treatment apparatus, etc.) of the users that used the treatment apparatus 70 or other treatment apparatuses to perform treatment plans, the details (e.g., treatment protocol including exercises, amount of time to perform the exercises, how often to perform the exercises, a schedule of exercises, parameters/configurations/settings of the treatment apparatus 70 throughout each step of the treatment plan, etc.) of the treatment plans performed by the users using the treatment apparatus 70, and the results of the treatment plans performed by the users. Further, the machine learning models 13 may be trained using a corpus of training data including inputs associated with characteristics of users and outputs associated with diagnosed medical conditions for the users. The machine learning models 13 may be trained using a corpus of training data including inputs associated with diagnosed medical conditions and outputs associated with treatment plans. The one or more machine learning models 13 may be trained to match patterns of characteristics of a patient with characteristics of other people assigned to a particular cohort. The term "match" may refer to an exact match, a positive or negative correlative match, a substantial match, etc. The one or more machine learning models 13 may be trained to receive the characteristics of a patient as input, map the characteristics to characteristics of people assigned to a cohort, and select a treatment plan from that cohort. The one or more machine learning models 13 may also be trained to control, based on the treatment plan, treatment apparatus 70. The one or more machine learning models 13 may also be trained to provide one or more treatment plan options to a healthcare professional to select from and to control the treatment apparatus 70.

Different machine learning models 13 may be trained to recommend different treatment plans for different desired results. For example, one machine learning model may be trained to recommend treatment plans for most effective recovery, while another machine learning model may be trained to recommend treatment plans based on speed of recovery.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.). In some embodiments, the patient interface 50 may include functionality provided by or similar to existing voice-based assistants such as Siri by Apple, Alexa by Amazon, Google Assistant, or Bixby by Samsung.

As generally illustrated in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment apparatus 70 may be any suitable medical, rehabilitative, therapeutic, etc. apparatus configured to be controlled distally via another computing device to treat a patient and/or exercise the patient. The treatment apparatus 70 may be an electromechanical machine including one or more weights, an electromechanical bicycle, an electromechanical spin-wheel, a smart-mirror, a treadmill, an interactive environment system or the like. The body part may include, for example, a spine, a hand, a foot, a knee, or a shoulder. The body part may include a part of a joint, a bone, or a muscle group, such as one or more vertebrae, a tendon, or a ligament. As generally illustrated in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 generally illustrated in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 generally illustrated in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 generally illustrated in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 generally illustrated in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 generally illustrated in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 a healthcare professional, such as those described herein, to remotely communicate with the patient interface 50 and/or the treatment apparatus 70. Such remote communications may enable the assistant to provide assistance or guidance to a patient using the system 10. More specifically, the assistant interface 94 is configured to communicate a telemedicine signal 96, 97, 98*a*, 98*b*, 99*a*, 99*b* with the patient interface 50 via a network connection such as, for example, via the first network 34 and/or the second network 58. The telemedicine signal 96, 97, 98*a*, 98*b*, 99*a*, 99*b* comprises one of an audio signal 96, an audiovisual signal 97, an interface control signal 98*a* for controlling a function of the patient interface 50, an interface monitor signal 98*b* for monitoring a status of the patient interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the healthcare professional may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the healthcare professional to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the healthcare professional. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the healthcare professional. In some embodiments, the system 10 may be configured to recognize and react to spoken requests or commands by the patient. For example, in response to a verbal command by the patient (which may be given in any one of several different languages), the system 10 may automatically initiate a telemedicine.

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for patients and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as an healthcare professional remotely from any conventional office infrastructure. Such remote work may be performed, for example, where the assistant interface 94 takes the form of a computer and/or telephone. This remote work functionality may allow for work-from-home arrangements that may include part time and/or flexible work hours for an healthcare professional.

Figure 2:
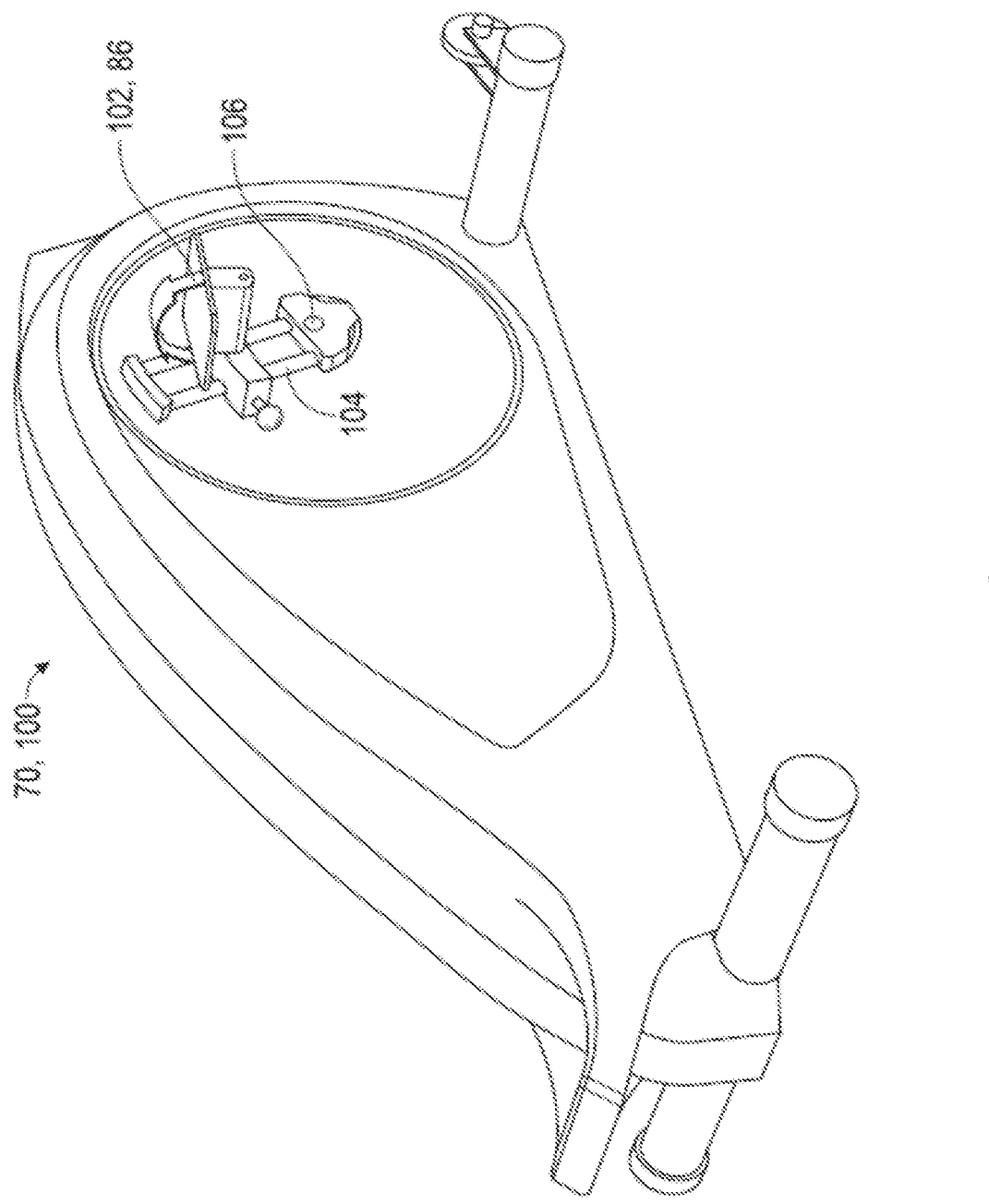
FIG. 2 generally illustrates a perspective view of an embodiment of a treatment apparatus according to the principles of the present disclosure.
Figure 3:
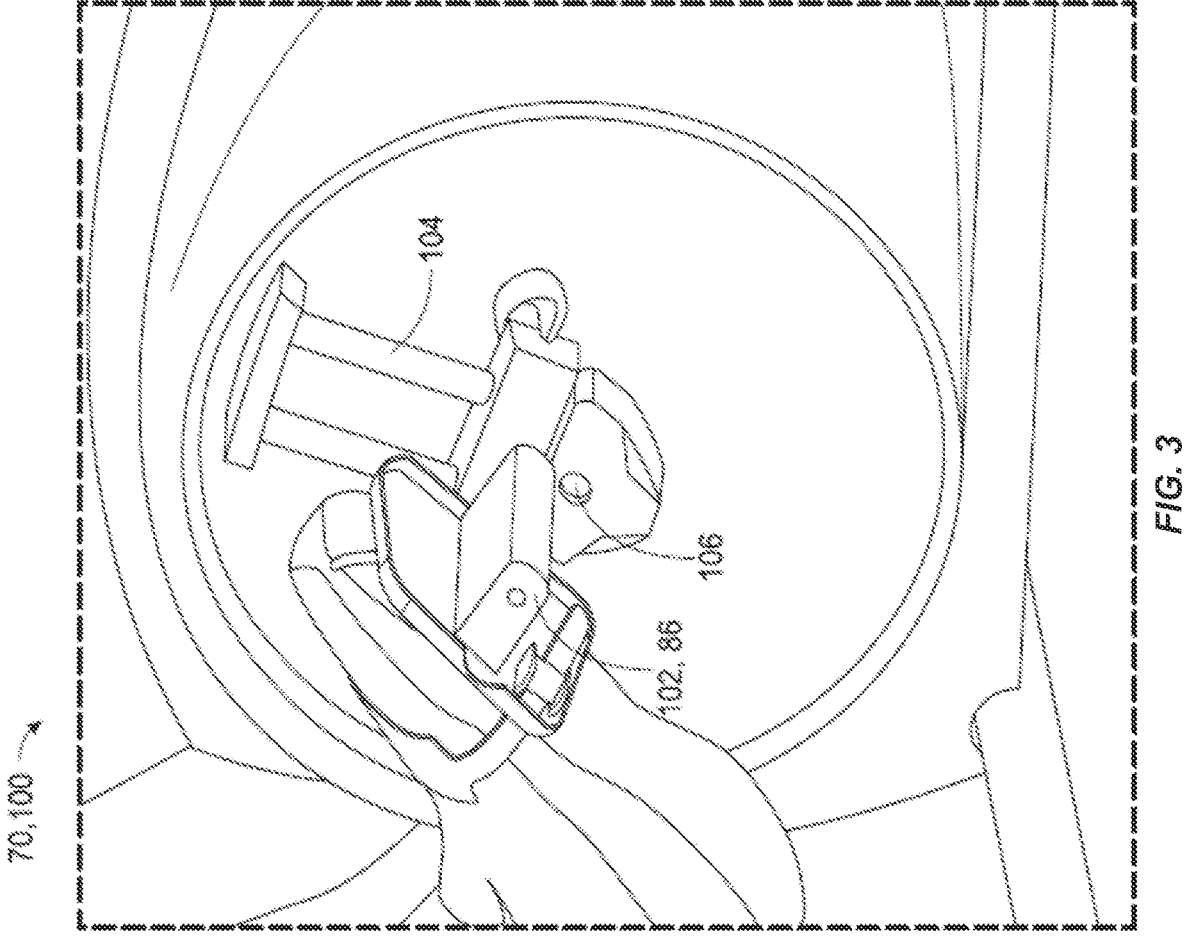
FIG. 3 generally illustrates a perspective view of a pedal of the treatment apparatus of FIG. 2 according to the principles of the present disclosure.

FIGS. 2-3 show an embodiment of a treatment apparatus 70. More specifically, FIG. 2 generally illustrates a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as generally illustrated in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. One or more pressure sensors 86 is attached to or embedded within one or both of the pedals 102 for measuring an amount of force applied by the patient on a pedal 102. The pressure sensor 86 may communicate wirelessly to the treatment apparatus 70 and/or to the patient interface 50.

Figure 4:
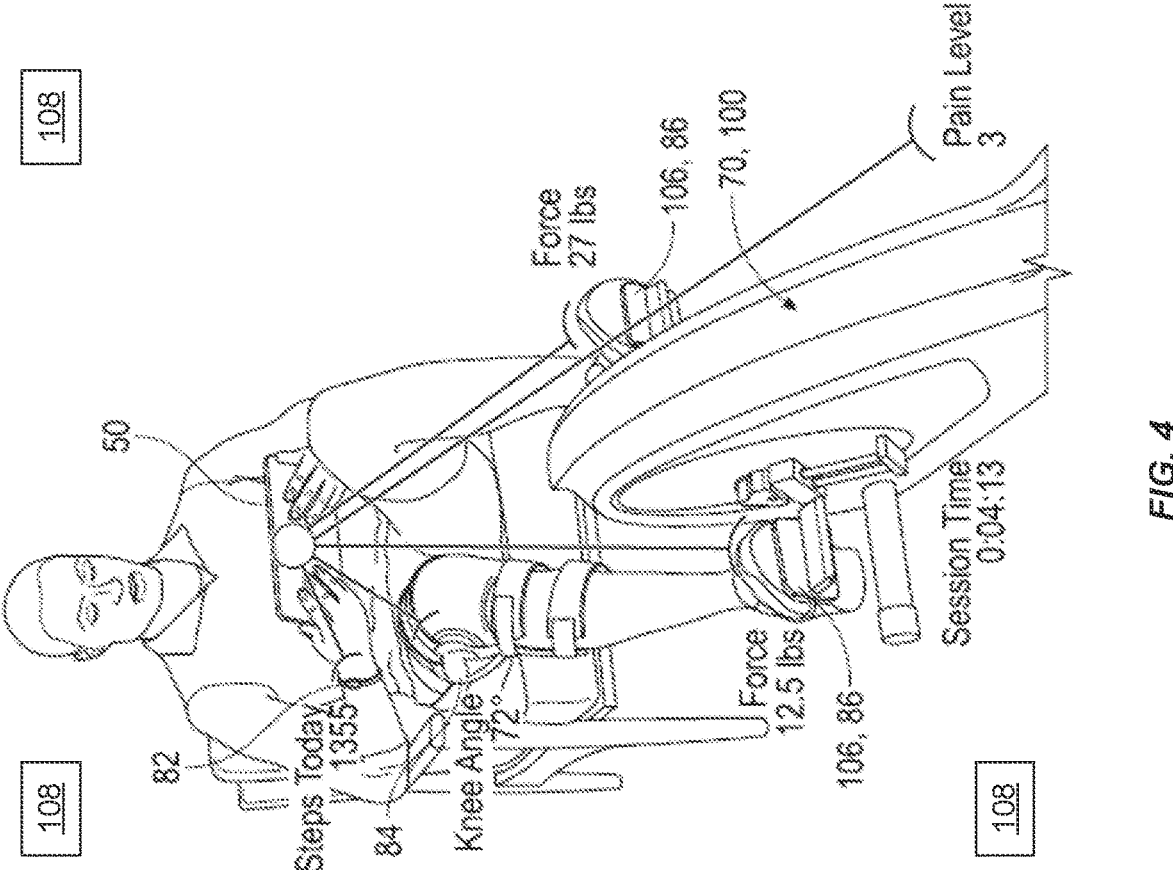
FIG. 4 generally illustrates a perspective view of a person using the treatment apparatus of FIG. 2 according to the principles of the present disclosure.

FIG. 4 generally illustrated a person (a patient) using the treatment apparatus of FIG. 2, and generally illustrating sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 generally illustrates the patient wearing the ambulation sensor 82 on his wrist, with a note showing "STEPS TODAY 1355", indicating that the ambulation sensor 82 has recorded and transmitted that step count to the patient interface 50. FIG. 4 also generally illustrates the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also generally illustrates an indicator showing "PAIN LEVEL 3". Such a pain level may be obtained from the patent in response to a solicitation, such as a question, presented upon the patient interface 50.

Additionally or alternatively, one of more remote sensing devices 108 may be located remotely (e.g., not in physical contact with the user) from the user for at least the purpose of detecting any suitable characteristic (e.g., vital signs, etc.) of the user. The one or more remote sensing devices 108 may include any suitable combination of the sensors shown in FIG. 4 and may be configured to remotely monitor the desired feedback. In some embodiments, the one or more remote sensing devices 108 may be located distally from the user, may be attached to the treatment apparatus 70, may be within a suitable range to enable wirelessly monitoring the desired feedback, and so forth. The one or more remote sensing devices 108 may include one or more cameras, thermal sensors, vibration sensors, auditory sensors, light sensors, etc. In some embodiments, the sensors may be configured to track eye movement of the user, determine one or more characteristics of the user's eyes (e.g., dilation, twitching, etc.), and so forth.

For example, the remote sensing devices 108 may include one or more high-definition cameras and/or an infrared cameras executing or communicatively coupled with one or more computing devices executing analytical software (e.g., motion-capture software and/or facial-recognition software). To detect a speed or number of repetitions that have been completed by the user using the treatment apparatus 70, the remote sensing devices 108 may also be configured to detect the location of at least one node, or marker, placed on the user or the treatment apparatus 70. For example, the remote sensing devices 108 may detect that the node attached to a right knee of the user moves sporadically (e.g. deviates from an expected motion) while the user uses the treatment apparatus 70. That is, based on virtually overlaying captured images and/or video of the knee's movement on the expected motion trajectory, it may be determined that an actual path of motion of the knee may deviate from an expected motion trajectory of the knee. In some embodiments, the remote sensing devices 108 may be configured to detect the temperature or perspiration of the user. In some embodiments, the remote sensing devices 108 may be configured to identify a level of strain the user undergoes while the user uses the treatment apparatus 70. For example, the one or more remote sensing devices 108 may execute computer instructions that implement facial recognition to detect a change in the physical appearance of the user (e.g., wrinkling of the skin around the user's eyes, clenching of the user's jaw), and, based on the change, a processing device may determine the level of strain the user is experiencing.

Figure 5:
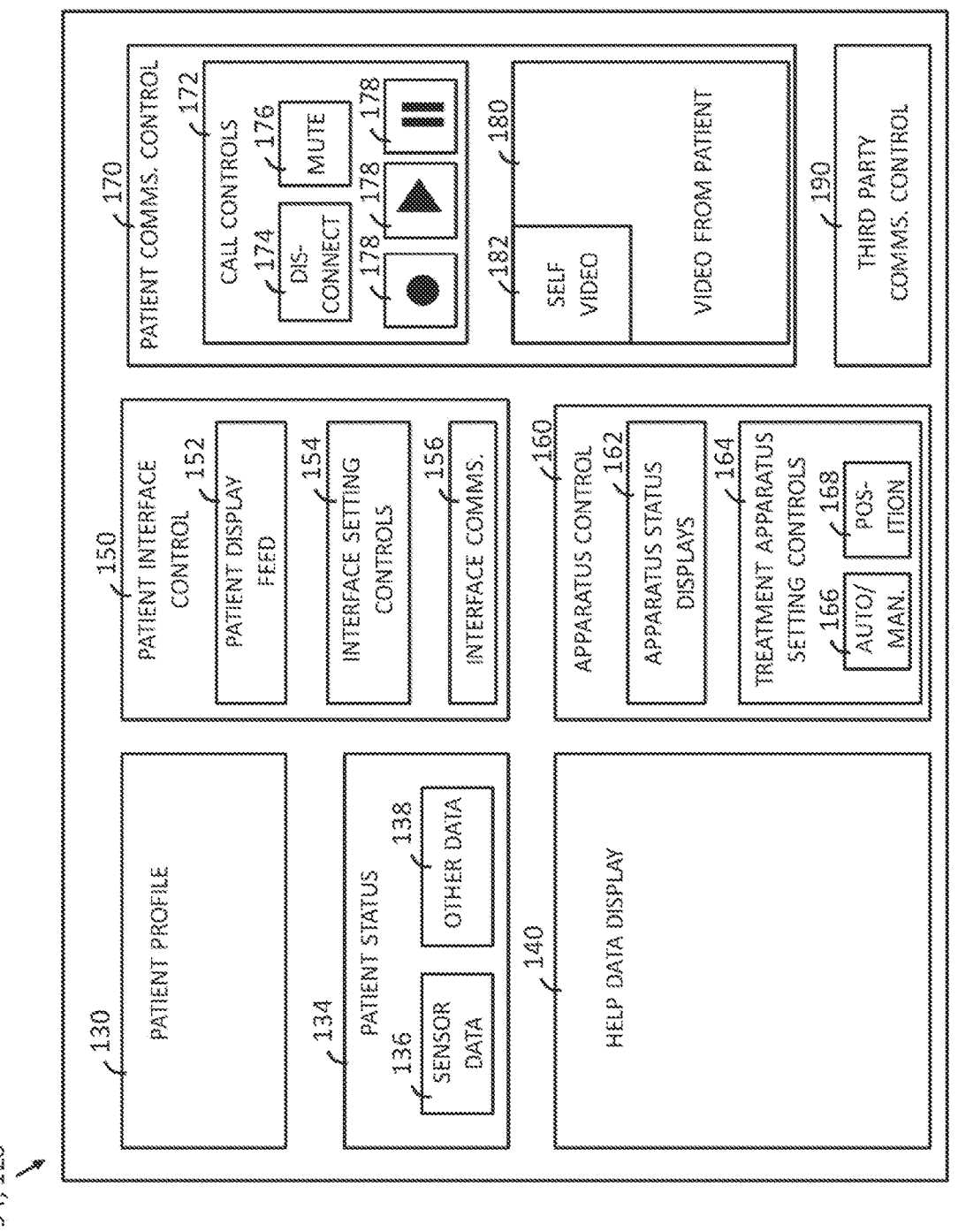
FIG. 5 generally illustrates an example embodiment of an overview display of an assistant interface according to the principles of the present disclosure.

FIG. 5 is an example embodiment of an overview display 120 of the assistant interface 94. Specifically, the overview display 120 presents several different controls and interfaces for the healthcare professional to remotely assist a patient with using the patient interface 50 and/or the treatment apparatus 70. This remote assistance functionality may also be called telemedicine or telehealth.

Specifically, the overview display 120 includes a patient profile display 130 presenting biographical information regarding a patient using the treatment apparatus 70. The patient profile display 130 may take the form of a portion or region of the overview display 120, as generally illustrated in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the healthcare professional's need for that information. For example, a healthcare professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonym zed data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment apparatus 70. Such treatment plan information may be limited to a healthcare professional. For example, a healthcare professional assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended treatment plans and/or excluded treatment plans may be presented in the patient profile display 130 to the healthcare professional. The one or more recommended treatment plans and/or excluded treatment plans may be generated by the artificial intelligence engine 11 of the server 30 and received from the server 30 in real-time during a telemedicine or telehealth session. An example of presenting the one or more recommended treatment plans and/or ruled-out treatment plans is described below with reference to FIG. 7.

The example overview display 120 generally illustrated in FIG. 5 also includes a patient status display 134 presenting status information regarding a patient using the treatment apparatus 70. The patient status display 134 may take the form of a portion or region of the overview display 120, as generally illustrated in FIG. 5, although the patient status display 134 may take other forms, such as those of a separate screen or a popup window. The patient status display 134 may include sensor data 136 from one or more of the external sensors 82, 84, 86, and/or from one or more internal sensors 76 of the treatment apparatus 70. In some embodiments, the patient status display 134 may include sensor data from one or more sensors of one or more wearable devices worn by the patient or spaced from the patient (i.e., the remote sensing devices 108) while the patient is using the treatment apparatus 70. The one or more wearable devices may include a watch, a bracelet, a necklace, a chest strap, and the like. The one or more wearable devices may be configured to monitor a heartrate, a temperature, a blood pressure, one or more vital signs, a blood oxygen level, a blood glucose level, and the like of the patient while the patient is using the treatment apparatus 70. To more accurately identify attributes of the user, the one or more remote sensing devices 108 may be configured to interact with or communicate with the wearable devices. For example, measurements obtained by the remote sensing devices 108 and the wearable devices may be compared with each other. If the measurements from the remote sensing devices 108 and the wearable devices match within a certain amount (e.g., percentage, specific number, specific value within a range of values, etc.), then a processing device may determine that the measurements are accurate. If the measurements from the remote sensing devices 108 and the wearable devices do not match within the certain amount, the processing device may determine that either the remote sensing devices 108 or the wearable devices are obtaining erroneous measurements, or that both are. In some embodiments, the processing device may recommend recalibrating the remote sensing devices and/or the wearable devices, resetting the remote sensing devices 108 and/or the wearable devices, or both. In some embodiments, the processing device may perform one or more control actions by electronically causing the remote sensing devices 108 and/or the wearable devices to recalibrate, reset, or both. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the healthcare professional/user's need for and/or qualifications to view that information.

The example overview display 120 generally illustrated in FIG. 5 also includes a help data display 140 presenting information for the healthcare professional to use in assisting the patient. The help data display 140 may take the form of a portion or region of the overview display 120, as generally illustrated in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the healthcare professional to use in determining a root cause and/or solution to a patient's problem. In some embodiments, the assistant interface 94 may present two or more help data displays 140, which may be the same or different, for simultaneous presentation of help data for use by the healthcare professional. for example, a first help data display may be used to present a troubleshooting flowchart to determine the source of a patient's problem, and a second help data display may present script information for the healthcare professional to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 generally illustrated in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98*b*. As generally illustrated in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the healthcare professional to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the healthcare professional to remotely view and/or control the patient interface 50. For example, the patient interface setting control 154 may enable the healthcare professional to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the healthcare professional to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the healthcare professional to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the healthcare professional to change the font size setting of the patient interface 50.

The example overview display 120 generally illustrated in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as generally illustrated in FIG. 5. The interface communications display 156 may take other forms, such as a separate screen or a popup window. The interface communications display 156 may include controls for the healthcare professional to remotely modify communications with one or more of the other devices 70, 82, 84. For example, the healthcare professional may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 generally illustrated in FIG. 5 also includes an apparatus control 160 for the healthcare professional to view and/or to control information regarding the treatment apparatus 70. The apparatus control 160 may take the form of a portion or region of the overview display 120, as generally illustrated in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99*b*. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the healthcare professional to adjust or control one or more aspects of the treatment apparatus 70. The apparatus setting control 164 may cause the assistant interface 94 to generate and/or to transmit an apparatus control signal 99 (e.g. which may be referred to as treatment plan input) for changing an operating parameter and/or one or more characteristics of the treatment apparatus 70, (e.g., a pedal radius setting, a resistance setting, a target RPM, other suitable characteristics of the treatment device 70, or a combination thereof). The apparatus setting control 164 may include a mode button 166 and a position control 168, which may be used in conjunction for the healthcare professional to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the healthcare professional may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the healthcare professional to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the healthcare professional to change the height or tilt setting of the treatment apparatus 70.

The example overview display 120 generally illustrated in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the healthcare professional while the healthcare professional uses the assistant interface 94. Alternatively or additionally, the audio and/or audiovisual communications may include communications with a third party. For example, the system 10 may enable the healthcare professional to initiate a 3-way conversation regarding use of a particular piece of hardware or software, with the patient and a subject matter expert, such as a medical professional or a specialist. The example patient communications control 170 generally illustrated in FIG. 5 includes call controls 172 for the healthcare professional to use in managing various aspects of the audio or audiovisual communications with the patient. The call controls 172 include a disconnect button 174 for the healthcare professional to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session (e.g., which may be referred to herein as the virtual conference room). The call controls 172 also include a video feed display 180 for presenting still and/or video images from the patient interface 94, and a self-video display 182 showing the current image of the healthcare professional using the assistant interface 94. The self-video display 182 may be presented as a picture-in-picture format, within a section of the video feed display 180, as generally illustrated in FIG. 5. Alternatively or additionally, the self-video display 182 may be presented separately and/or independently from the video feed display 180.

The example overview display 120 generally illustrated in FIG. 5 also includes a third party communications control 190 for use in conducting audio and/or audiovisual communications with a third party. The third party communications control 190 may take the form of a portion or region of the overview display 120, as generally illustrated in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a healthcare professional or a specialist. The third party communications control 190 may include conference calling capability for the third party to simultaneously communicate with both the healthcare professional via the assistant interface 94, and with the patient via the patient interface 50. For example, the system 10 may provide for the healthcare professional to initiate a 3-way conversation with the patient and the third party.

Figure 6:
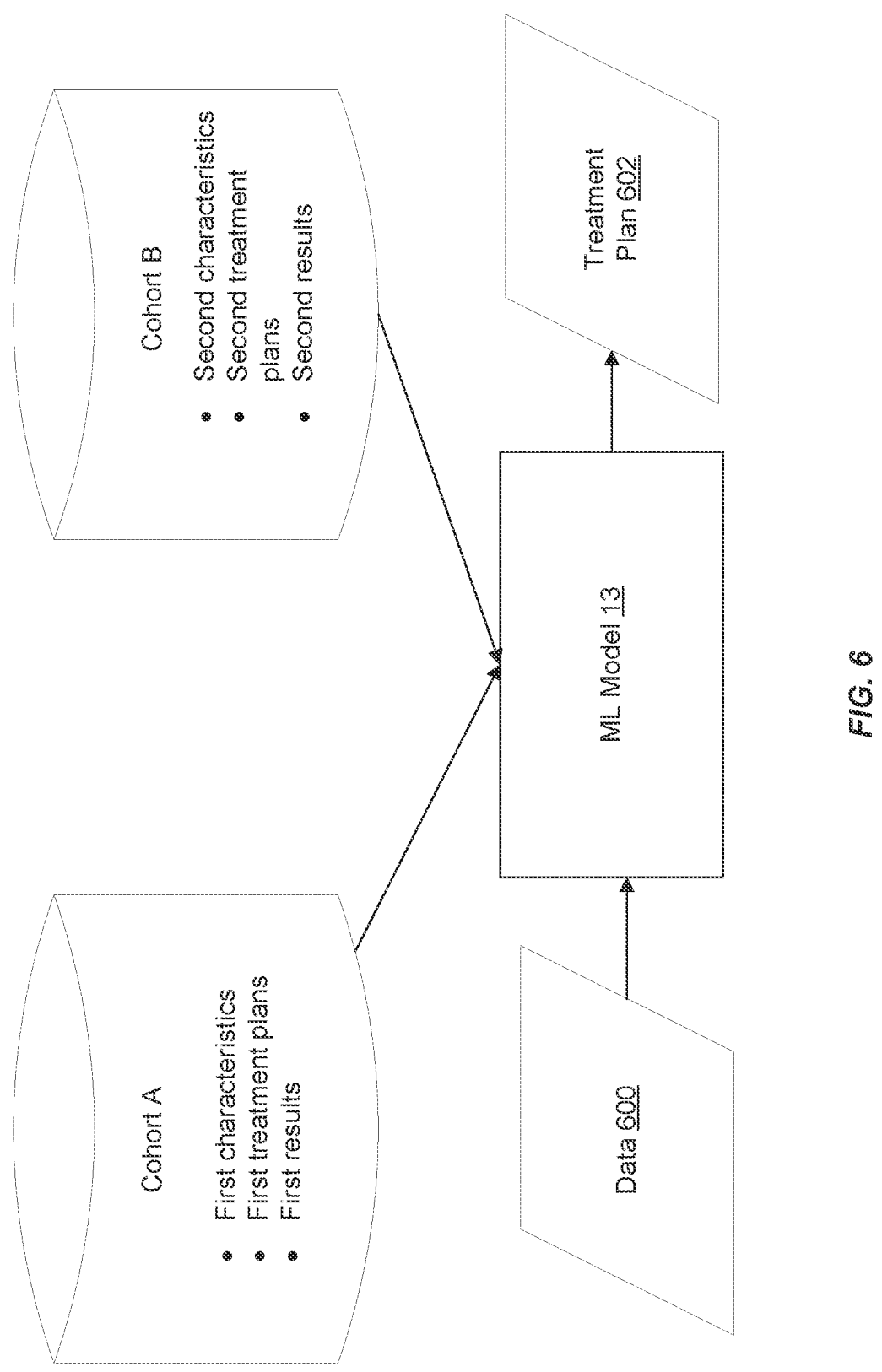
FIG. 6 generally illustrates an example block diagram of training a machine learning model to output, based on data pertaining to the patient, a treatment plan for the patient according to the principles of the present disclosure.

FIG. 6 generally illustrates an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the treatment apparatus 70 for 30 minutes 5 times a week for 3 weeks, wherein values for the properties, configurations, and/or settings of the treatment apparatus 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan or a variety of possible treatment plans for selection by a healthcare provider that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan or plans 602. In some embodiments, the machine learning model 13 may be trained to output one or more excluded treatment plans that should not be performed by the new patient.

FIG. 7 generally illustrates an embodiment of an overview display 120 of the assistant interface 94 presenting recommended treatment plans and excluded treatment plans in real-time during a telemedicine session according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

The healthcare professional using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the healthcare professional to share, in real-time or near real-time during the telemedicine session, the recommended treatment plans and/or the excluded treatment plans with the patient on the patient interface 50. The healthcare professional may select the GUI object 700 to share the recommended treatment plans and/or the excluded treatment plans. As depicted, another portion of the overview display 120 includes the patient profile display 130.

The patient profile display 130 is presenting two example recommended treatment plans 600 and one example excluded treatment plan 602. As described herein, the treatment plans may be recommended in view of characteristics of the patient being treated. To generate the recommended treatment plans 600 the patient should follow to achieve a desired result, a pattern between the characteristics of the patient being treated and a cohort of other people who have used the treatment apparatus 70 to perform a treatment plan may be matched by one or more machine learning models 13 of the artificial intelligence engine 11. Each of the recommended treatment plans may be generated based on different desired results.

For example, as depicted, the patient profile display 130 presents "The characteristics of the patient match characteristics of users in Cohort A. The following treatment plans are recommended for the patient based on his characteristics and desired results." Then, the patient profile display 130 presents recommended treatment plans from cohort A, and each treatment plan provides different results.

As depicted, treatment plan "A" indicates "Patient X should use treatment apparatus for 30 minutes a day for 4 days to achieve an increased range of motion of Y %; Patient X has Type 2 Diabetes; and Patient X should be prescribed medication Z for pain management during the treatment plan (medication Z is approved for people having Type 2 Diabetes)." Accordingly, the treatment plan generated achieves increasing the range of motion of Y %. As may be appreciated, the treatment plan also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome. This specific example and all such examples elsewhere herein are not intended to limit in any way the generated treatment plan from recommending multiple medications, or from handling the acknowledgement, view, diagnosis and/or treatment of comorbid conditions or diseases.

Recommended treatment plan "B" may specify, based on a different desired result of the treatment plan, a different treatment plan including a different treatment protocol for a treatment apparatus, a different medication regimen, etc.

As depicted, the patient profile display 130 may also present the excluded treatment plans 602. These types of treatment plans are shown to the healthcare professional using the assistant interface 94 to alert the healthcare professional not to recommend certain portions of a treatment plan to the patient. For example, the excluded treatment plan could specify the following: "Patient X should not use treatment apparatus for longer than 30 minutes a day due to a heart condition; Patient X has Type 2 Diabetes; and Patient X should not be prescribed medication M for pain management during the treatment plan (in this scenario, medication M can cause complications for people having Type 2 Diabetes). Specifically, the excluded treatment plan points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

The healthcare professional may select the treatment plan for the patient on the overview display 120. For example, the healthcare professional may use an input peripheral (e.g., mouse, touchscreen, microphone, keyboard, etc.) to select from the treatment plans 600 for the patient. In some embodiments, during the telemedicine session, the healthcare professional may discuss the pros and cons of the recommended treatment plans 600 with the patient.

In any event, the healthcare professional may select the treatment plan for the patient to follow to achieve the desired result. The selected treatment plan may be transmitted to the patient interface 50 for presentation. The patient may view the selected treatment plan on the patient interface 50. In some embodiments, the healthcare professional and the patient may discuss during the telemedicine session the details (e.g., treatment protocol using treatment apparatus 70, diet regimen, medication regimen, etc.) in real-time or in near real-time. In some embodiments, the server 30 may control, based on the selected treatment plan and during the telemedicine session, the treatment apparatus 70 as the user uses the treatment apparatus 70.

FIG. 8 generally illustrates an embodiment of the overview display 120 of the assistant interface 94 presenting, in real-time during a telemedicine session, recommended treatment plans that have changed as a result of patient data changing according to the present disclosure. As may be appreciated, the treatment apparatus 70 and/or any computing device (e.g., patient interface 50) may transmit data while the patient uses the treatment apparatus 70 to perform a treatment plan. The data may include updated characteristics of the patient and/or other treatment data. For example, the updated characteristics may include new performance information and/or measurement information. The performance information may include a speed of a portion of the treatment apparatus 70, a range of motion achieved by the patient, a force exerted on a portion of the treatment apparatus 70, a heartrate of the patient, a blood pressure of the patient, a respiratory rate of the patient, and so forth.

In some embodiments, the data received at the server 30 may be input into the trained machine learning model 13, which may determine that the characteristics indicate the patient is on track for the current treatment plan. Determining the patient is on track for the current treatment plan may cause the trained machine learning model 13 to adjust a parameter of the treatment apparatus 70. The adjustment may be based on a next step of the treatment plan to further improve the performance of the patient.

In some embodiments, the data received at the server 30 may be input into the trained machine learning model 13, which may determine that the characteristics indicate the patient is not on track (e.g., behind schedule, not able to maintain a speed, not able to achieve a certain range of motion, is in too much pain, etc.) for the current treatment plan or is ahead of schedule (e.g., exceeding a certain speed, exercising longer than specified with no pain, exerting more than a specified force, etc.) for the current treatment plan. The trained machine learning model 13 may determine that the characteristics of the patient no longer match the characteristics of the patients in the cohort to which the patient is assigned. Accordingly, the trained machine learning model 13 may reassign the patient to another cohort that includes qualifying characteristics the patient's characteristics. As such, the trained machine learning model 13 may select a new treatment plan from the new cohort and control, based on the new treatment plan, the treatment apparatus 70.

In some embodiments, prior to controlling the treatment apparatus 70, the server 30 may provide the new treatment plan 800 to the assistant interface 94 for presentation in the patient profile 130. As depicted, the patient profile 130 indicates "The characteristics of the patient have changed and now match characteristics of users in Cohort B. The following treatment plan is recommended for the patient based on his characteristics and desired results." Then, the patient profile 130 presents the new treatment plan 800 ("Patient X should use the treatment apparatus for 10 minutes a day for 3 days to achieve an increased range of motion of L %" The healthcare professional may select the new treatment plan 800, and the server 30 may receive the selection. The server 30 may control the treatment apparatus 70 based on the new treatment plan 800. In some embodiments, the new treatment plan 800 may be transmitted to the patient interface 50 such that the patient may view the details of the new treatment plan 800.

FIG. 9 is a flow diagram generally illustrating a method 900 for updating a treatment plan associated with a user using a treatment apparatus according to the principles of the present disclosure. The method 900 is performed by processing logic that may include hardware (circuitry, dedicated logic, etc.), software (such as is run on a general-purpose computer system or a dedicated machine), or a combination of both. The method 900 and/or each of its individual functions, routines, subroutines, methods (e.g., object-oriented programming), or operations may be performed by one or more processors of a computing device (e.g., any component of FIG. 1, such as server 30 executing the artificial intelligence engine 11). In some embodiments, the method 900 may be performed by a single processing thread. Alternatively, the method 900 may be performed by two or more processing threads, each thread implementing one or more individual functions, routines, subroutines, object-oriented methods, or operations of the methods.

For simplicity of explanation, the method 900 is depicted and described as a series of operations. However, operations in accordance with this disclosure can occur in various orders and/or concurrently, and/or with other operations not presented and described herein. For example, the operations depicted in the method 900 may occur in combination with any other operation of any other method disclosed herein. Furthermore, not all illustrated operations may be required to implement the method 900 in accordance with the disclosed subject matter. In addition, those skilled in the art will understand and appreciate that the method 900 could alternatively be represented as a series of interrelated states via a state diagram or event diagram.

In some embodiments, one or more machine learning models 13 may be generated and trained by the artificial intelligence engine 11 and/or the training engine 9 to perform one or more of the operations of the method 900. For example, to perform the one or more operations, the processing device may execute the one or more machine learning models 13. In some embodiments, the one or more machine learning models 13 may be iteratively retrained to select different features capable of enabling optimization of output. The features that may be modified may include a number of nodes included in each layer of the machine learning models 13, an objective function executed at each node, a number of layers, various weights associated with outputs of each node, and the like.

At 902, the processing device may receive first data associated with a first diagnosis of the user. For example, the first data may be received from one or more electronic medical record systems, the server 30, one or more user interfaces, the memory 38, the first network 34, the second network 58, the data source 15, the treatment apparatus 70, one or more sensors attached to the user, one or more wearable devices, one or more remote sensing devices 108, or any other suitable device part of or in communication with the processing device or treatment apparatus 70. The first data may include one or more diagnostics codes, healthcare professional notes regarding the user, etc.

At 904, the processing device may generate, based on the first data, an initial treatment plan to be performed on the treatment apparatus 70 by the user. In some embodiments, the first diagnosis may be a physiological condition, such as a torn anterior cruciate ligament (ACL), and the user may be recovering from a surgery. In some embodiments, the first diagnosis may be a neurological condition, such as Parkinson's disease. In some embodiments, the first diagnosis may be a cardiac or vascular condition, such as myocarditis, aortic stenosis, atherosclerosis, hypertension, or Raynaud's Disease. The initial treatment plan may be generated by one or more machine learning models 13 trained to receive the first data as input and to output the initial treatment plan. For example, the one or more machine learning models 13 may be trained to map a pattern of the first data to other data of users in a cohort and to assign the user to the cohort. Based on the assigned cohort, the one or more machine learning models 13 may generate and output the initial treatment plan for the user. The initial treatment plan may include one or more exercises and one or more operating parameters, etc., wherein the one or more exercises and/or the one or more operating parameters and the like are tailored to treat and/or achieve a desired goal associated with the first diagnosis.

At 906, the processing device may receive second data associated with a first attribute of the user. In some embodiments, the first attribute may be sensor data received from one or more sensors associated with the user. In some embodiments, the second data may be received in real-time or near real-time. In some embodiments, the second data may be associated with an amount of time the user takes to respond to a stimulus. In some embodiments, the stimulus may include at least one of an audio, a visual, and a haptic stimulus provided to the user. The audio stimulus may include an audio characteristic associated with at least one of a volume, a cadence, a tone, an enunciation, a word, a language, a dialect, a vernacular, an accent, an emphasis, a pitch, a rhythm, an order of words, a tense, a timbre, and a prosody. The visual stimulus may include a visual characteristic associated with at least one of a color, an image, a video, a text, a font type, a font style, a point size, a font modifier, a virtual-reality environment, and an illumination. The haptic stimulus may include a haptic characteristic associated with at least one of a vibration, a force, a pressure, a torque, an intensity, a resistance, an electric stimulus, an ultrasonic frequency, a heat level, and a temperature.

In some embodiments, the sensor data may include at least one of a measurement of a vital sign of the user, a respiration rate of the user, a heartrate of the user, a heart rhythm of a user, an oxygen saturation level (e.g., SpO2) of the user, a sugar level of the user, a composition of blood of the user, a cerebral activity of the user, a cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the treatment apparatus, an amount of force exerted on a portion of the treatment apparatus, a range of motion achieved on the treatment apparatus, a speed measurement of a moving portion of the treatment apparatus, a pressure exerted on a portion of the exercise apparatus, an acceleration measurement of a moving portion of the exercise apparatus, a jerk of a portion of the exercise apparatus, a torque level of a portion of the exercise apparatus, and an indication of a plurality of pain levels experienced by the user when using the treatment apparatus.

Figure 10:
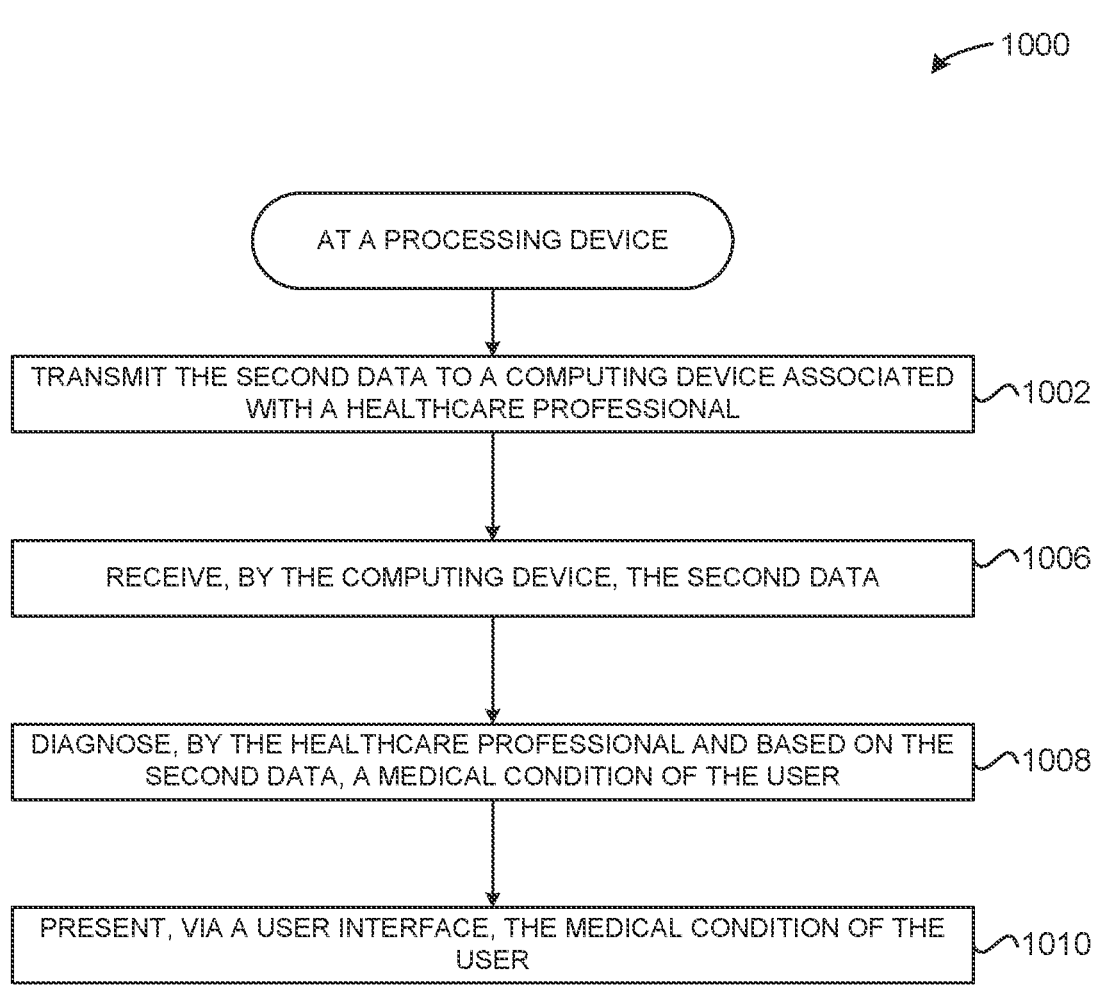
FIG. 10 is a flow diagram generally illustrating a method for a healthcare professional diagnosing a medical condition of a user according to the principles of the present disclosure.
Figure 11:
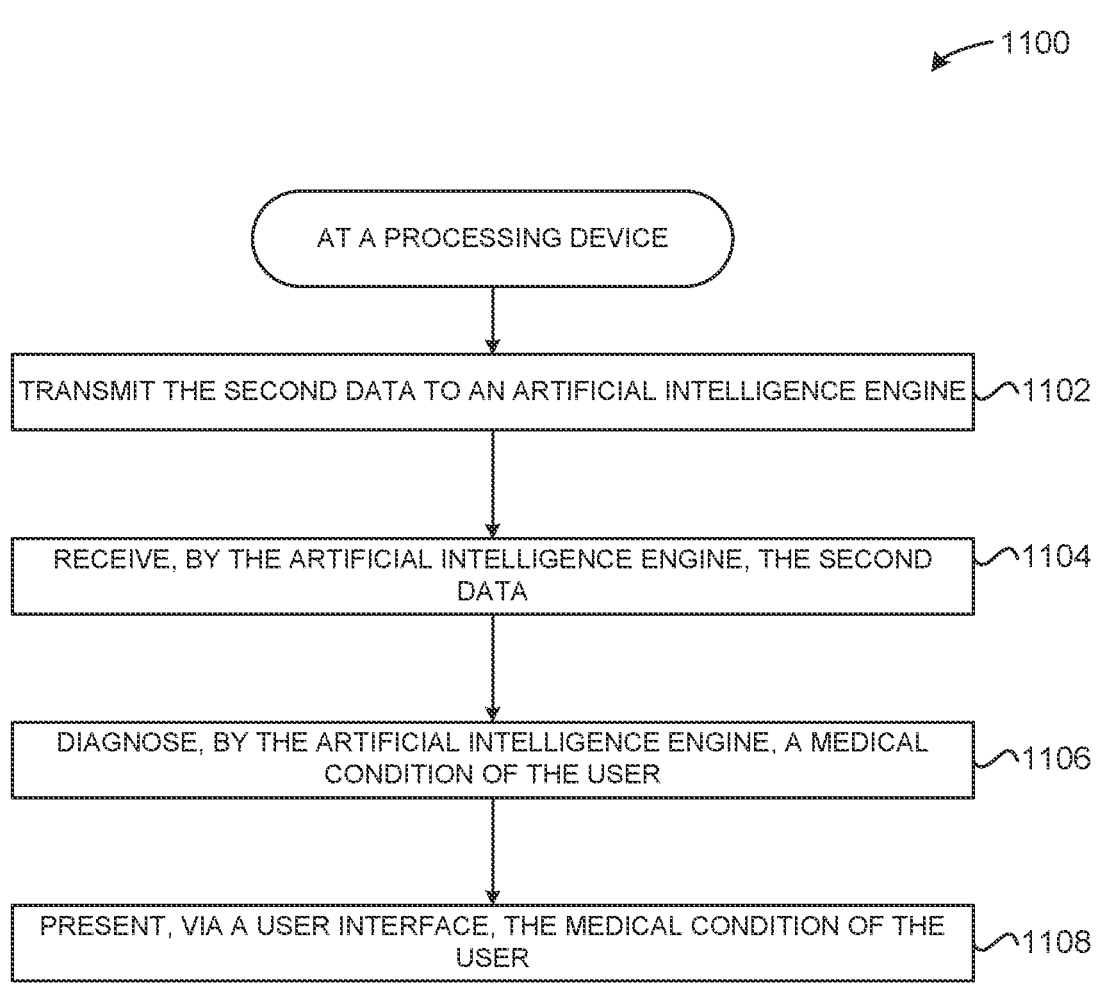
FIG. 11 is a flow diagram generally illustrating a method for an artificial intelligence engine diagnosing a medical condition of a user according to the principles of the present disclosure.

In some embodiments, as described further herein with reference to FIGS. 10 and 11, the processing device may determine, based on the second data, a first condition of the user. The first condition may include a neurological condition that affects a function of the user, such as a somatic function, a psychological function, a behavioral function, a dexterity function, a cerebral function, a physiological function, an anatomical function, a cardiac function, a neurological function, an endocrinological function, or some combination thereof. In some embodiments, the first condition of the user may be included (e.g., added, appended, concatenated, etc.) in the second data.

At 908, the processing device may generate, via an artificial intelligence engine 11, a machine learning model 13 trained to generate an updated treatment plan for the user, wherein the updated treatment plan is based on the initial treatment plan, the second data, the first attribute, and/or the first condition. In some embodiments, the first attribute may be a second diagnosis of the user. For example, the second diagnosis may be received from one or more application programming interfaces and/or databases associated with one or more electronic medical record systems, computing devices of a healthcare professional, or the like. In some embodiments, at least one of the first and the second diagnoses may be a medical diagnosis made by a healthcare professional and/or the artificial intelligence engine 11. For example, the user may visit a location (e.g., clinic, office, hospital, etc.) where the healthcare professional practices and the user may undergo one or more mental and/or physical tests and/or evaluations. Further, bloodwork of the user may be obtained and assayed and/or tested. Based on the results of the mental tests and/or evaluations, the physical tests and/or evaluations, and/or the bloodwork results, the healthcare professional may generate the first and/or second diagnoses of the user.

In some embodiments, one or more of the first and second diagnoses may include at least a neurological condition. The neurological condition may include, for example, Alzheimer's disease, amyotrophic lateral sclerosis (ALS), Parkinson's disease, myasthenia gravis, multiple sclerosis, attention deficit hyperactivity disorder (ADHD), attention deficit disorder (ADD), aphasias, dysautonomias, phantom limb syndrome, arthritis, and conditions arising from a disease or injury, such as a spinal cord injury, fall injury, and a stroke. In some embodiments, the neurological condition may affect a function of the user. The function may include aE somatic function, a psychological function, a behavioral function, a dexterity function, a cerebral function, a physiological function, an anatomical function, a cardiac function, a neurological function, an endocrinological function, or some combination thereof.

At 910, the processing device may control, based on the updated treatment plan, the treatment apparatus 70. In some embodiments, the processing device may transmit one or more control instructions to the treatment apparatus 70. The control instructions may be received by a network interface of the treatment apparatus 70 and transmitted to a processing device of the treatment apparatus 70. The processing device of the treatment apparatus 70 may execute the control instructions to implement one or more operating parameters associated with an aspect of the updated treatment plan. For example, the updated treatment plan may specify a range of motion (e.g., operating parameter) for the user to actuate when using one or more pedals of the treatment apparatus 70 to treat a symptom of the neurological condition. The control instructions may cause the pedals of the treatment apparatus 70 to move to a physical setting or physical settings that provide the desired range of motion. The pedal adjustments may be bilaterally symmetric or asymmetric. Any suitable operating parameter of the treatment apparatus 70 may be modified in real-time or near real-time. Such modifications to a suitable operating parameter may also be bilaterally symmetric or asymmetric.

In some embodiments, the initial treatment plan may be based solely on a first condition and a characteristic of the patient, such as age or weight. The updated treatment plan, however, may incorporate an additional, generally unrelated, condition of the user. For example, the additional condition may be a second diagnosis associated with the user (e.g., neuropathy in the user's wrist), while the first condition may be related to a physical injury, such as a torn anterior cruciate ligament (ACL). Because the symptoms of these two conditions may generally be unrelated, the effects of these two conditions (comorbidities) may not be factored into a treatment plan for implementation on a treatment apparatus 70. The updated treatment plan, however, may utilize a generated machine learning model 13 to optimize the treatment plan for the user with these two conditions. As a result, in this example, the treatment apparatus 70 may be utilized to treat/compensate for the second condition. This may include correlating data associated with other users having the same second condition. For example, the machine learning model may assign the user to a cohort of the users having the same second condition, and the updated treatment plan may be generated to treat/compensate for the second condition.

In an alternative form of the above example, the second condition, such as a first attribute of the user, may be identified by the server 30 (e.g., via one or more machine learning models 13). As such, the machine learning model 13 may identify a diagnosis previously unidentified by a healthcare professional and also update the treatment plan based on that diagnosis. For example, by utilizing various sensors and remote sensing devices 108 associated with the user using the treatment apparatus 70, a response time of the user may be ascertained. Continuing with the example, data corresponding to the response time may be transmitted to the server 30. The server 30 may then process that data and correlate the data with a medical diagnosis. The medical diagnosis can include a diagnosis that encompasses comorbidities. Accordingly, in this example, one or more machine learning models 13 may effectively diagnose a medical condition of the user. Concurrent with identifying the diagnosis, the server 30 may update the treatment plan based on one or more diagnoses and the initial treatment plan.

FIG. 10 is a flow diagram generally illustrating a method 1000 for a healthcare professional diagnosing a medical condition of a user according to the principles of the present disclosure. Method 1000 includes operations performed by processors of a computing device (e.g., any component of FIG. 1, such as server 30 executing the artificial intelligence engine 11). In some embodiments, one or more operations of the method 1000 are implemented in computer instructions stored on a memory device and executed by a processing device. The method 1000 may be performed in the same or a similar manner as described above in regard to method 900. The operations of the method 1000 may be performed in some combination with any of the operations of any of the methods described herein.

In some embodiments, to perform one or more of the operations of the method 1000, one or more machine learning models 13 may be generated and trained by the artificial intelligence engine 11 and/or the training engine 9. For example, to perform the one or more operations, the processing device may execute the one or more machine learning models 13. In some embodiments, the one or more machine learning models 13 may be iteratively retrained to select different features capable of enabling optimization of output. The features that may be modified may include a number of nodes included in each layer of the machine learning models 13, an objective function executed at each node, a number of layers, various weights associated with outputs of each node, and the like.

In some embodiments, the processing device may determine, based on the second data, a first condition of the user. In some embodiments, the processing device may determine the first condition of the user by transmitting, at 1002, the second data to a computing device associated with a healthcare professional. At 1004, the computing device associated with the healthcare professional may receive the second data. The second data may be presented on a user interface of the computing device associated with the healthcare professional. At 1006, the healthcare professional may diagnose, based on the second data, a medical condition of the user. The medical condition can include a condition that encompasses comorbidities. Various graphical elements may be presented in the user interface that enable the healthcare professional to select or enter a medical condition diagnosed for the user. In some embodiments, the medical condition of the user may be the first condition.

Further, after the healthcare professional selects or enters the medical condition diagnosed for the user, an updated treatment plan may be generated by the artificial intelligence engine 11. The updated treatment plan may be presented on the user interface of a computing device associated with the healthcare professional. The healthcare professional may use one or more graphical elements on the user interface to select the updated treatment plan. To modify one or more operating parameters in accordance with an aspect of the updated treatment plan 70, the selected updated treatment plan may control the treatment apparatus 70.

FIG. 11 is a flow diagram generally illustrating a method 1100 for an artificial intelligence engine diagnosing a medical condition of a user according to the principles of the present disclosure. Method 1100 includes operations performed by processors of a computing device (e.g., any component of FIG. 1, such as server 30 executing the artificial intelligence engine 11). In some embodiments, one or more operations of the method 1100 are implemented in computer instructions stored on a memory device and executed by a processing device. The method 1100 may be performed in the same or a similar manner as described above in regard to method 900 and/or method 1000. The operations of the method 1100 may be performed in some combination with any of the operations of any of the methods described herein.

In some embodiments, one or more machine learning models 13 may be generated and trained by the artificial intelligence engine 11 and/or the training engine 9 to perform one or more of the operations of the method 1100. For example, to perform the one or more operations, the processing device may execute the one or more machine learning models 13. In some embodiments, the one or more machine learning models 13 may be iteratively retrained to select different features capable of enabling optimization of output. The features that may be modified may include a number of nodes included in each layer of the machine learning models 13, an objective function executed at each node, a number of layers, various weights associated with outputs of each node, and the like.

In some embodiments, the processing device may determine, based on the second data, a first condition of the user. In some embodiments, the processing device may determine the first condition of the user by transmitting, at 1102, the second data to the artificial intelligence engine 11. At 1104, the artificial intelligence engine 11 may receive the second data. At 1106, the artificial intelligence engine 11 may diagnose, based on the second data, a medical condition of the user. The medical condition can include a condition that encompasses comorbidities. In some embodiments, the medical condition of the user may be the first condition.

In some embodiments, the artificial intelligence engine 11 may generate and train one or more machine learning models 13 to diagnose the medical condition of the user. For example, the artificial intelligence engine 11 may use a training engine 9 to train the machine learning models 13 using a corpus of training data that includes data pertaining to users (e.g., attributes of the users, medical histories of the users, familial medical histories of the users, measurements of vital signs of the users, respiration rates of the users, heartrates of the users, heart rhythms of the users, oxygen saturation levels of the users, sugar levels of the users, compositions of blood of the users, cerebral activities of the users, cognitive activities of the users, lung capacities of the users, temperatures of the users, blood pressures of the users, eye movements of the users, degrees of dilation of eyes of the users, reaction times, sounds produced by the users, perspiration rates of the users, elapsed times of using the treatment apparatuses, amounts of force exerted on one or more portions of the treatment apparatuses, ranges of motion achieved on the treatment apparatuses, speed measurements of one or more moving portions of the treatment apparatuses, pressures exerted on one or more portions of the exercise apparatuses, acceleration measurements of one or more moving portions of the exercise apparatuses, jerks of one or more portions of the exercise apparatuses, torque levels of one or more portions of the exercise apparatuses, indications of one or more pain levels experienced by the users when using the treatment apparatuses, etc.) mapped to outputs associated with medical condition diagnoses of the users.

Accordingly, once trained, the one or more machine learning models 13 may receive the second data as input and output the medical condition diagnosis of the user. In some embodiments, the artificial intelligence engine 9 may continuously receive new data pertaining to the users from electronic medical record systems, databases, computing devices, etc. and new medical condition diagnoses. The artificial intelligence engine 11 may retrain the machine learning models 13 based on the subsequently received data and medical condition diagnoses. In some embodiments, the artificial intelligence engine 11 may receive one or more indications that a medical condition diagnosis generated by a machine learning model 13 is correct or, alternatively, that it is wrong or excludable. The one or more indications may be provided by a computing device of a healthcare professional. The one or more indications may cause the artificial intelligence engine 11 to retrain the one or more machine learning models 13 to adjust one or more features to account for the one or more indications. The one or more features may include a number of hidden layers of the machine learning models 13, a number of nodes included in each of the hidden layers, an activation function associated with each layer, a weight associated with each node of each layer, and the like.

FIG. 12 generally illustrates an embodiment of the overview display 120 of the assistant interface 94 presenting, in real-time during a telemedicine session, an updated treatment plan based on a diagnosed medical condition of the user according to the principles of the present disclosure. The medical condition can include a condition that encompasses comorbidities. As may be appreciated, while the patient uses the treatment apparatus 70 to perform a treatment plan, the treatment apparatus 70 and/or any computing device (e.g., patient interface 50) may transmit data. The data may include updated second data, such as characteristics of the patient and/or other treatment data.

For example, the updated characteristics may include new performance information and/or measurement information. The information may include a vital sign of the user, a respiration rate of the user, a heartrate of the user, a heart rhythm of a user, an oxygen saturation level of the user, a sugar level of the user, a composition of blood of the user, a cerebral activity of the user, a cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the treatment apparatus, an amount of force exerted on a portion of the treatment apparatus, a range of motion achieved on the treatment apparatus, a speed measurement of a moving portion of the treatment apparatus, a pressure exerted on a portion of the exercise apparatus, an acceleration measurement of a moving portion of the exercise apparatus, a jerk of a portion of the exercise apparatus, a torque level of a portion of the exercise apparatus, an indication of a plurality of pain levels experienced by the user when using the treatment apparatus, and so forth.

In some embodiments, the second data received at the server 30 may be input into the trained machine learning model 13, which may generate, based on an initial treatment plan for the user and the second data, an updated treatment plan. In some embodiments, the machine learning model 13 and/or a healthcare professional may use the second data to diagnose a medical condition of the user. The medical condition diagnosis may include Alzheimer's disease, amyotrophic lateral sclerosis (ALS), Parkinson's disease, myasthenia gravis, multiple sclerosis, attention deficit hyperactivity disorder (ADHD), attention deficit disorder (ADD), aphasias, dysautonomias, phantom limb syndrome, arthritis, and conditions arising from a disease or injury, such as a spinal cord injury, fall injury, and a stroke. In some embodiments, the neurological condition may affect a function of the user. Examples of such functions which may be included comprise: a somatic function, a psychological function, a behavioral function, a dexterity function, a cerebral function, a physiological function, an anatomical function, a cardiac function, a neurological function, an endocrinological function, or some combination thereof.

Generating the updated treatment plan for the user may cause the trained machine learning model 13 to adjust an operating parameter of the treatment apparatus 70. The adjustment may be based on a step of the updated treatment plan to treat a symptom of the medical condition diagnosed for the user. For example, if the diagnosis indicates the user has Parkinson's disease, then the user may exhibit a tremor in a limb as a symptom of Parkinson's disease. In one example, research may indicate that performing sprint exercises using the treatment apparatus 70 reduces the tremor symptom. In other instances, research may indicate that, e.g., performing sprint exercises ameliorates or eliminates the underlying cause of the symptoms, rather than just the symptoms or only the symptoms. Accordingly, the updated treatment plan may include operating parameters that enable performing a sprint (e.g., high motor pedaling speed for a short duration of time).

In some embodiments, prior to controlling the treatment apparatus 70, the server 30 may provide the updated treatment plan 1200 to the assistant interface 94 for presentation in the patient profile 130. Further, a medical condition 1202 diagnosed for the user may be presented in the patient profile 130. As depicted, the patient profile 130 indicates "Neurological medical condition: Parkinson's disease." The updated treatment plan 1200 indicates "The characteristics of the patient have changed and now match relevant characteristics of users in Cohort B. The following treatment plan is recommended for the patient based on his characteristics and desired results." Then, the patient profile 130 presents the new treatment plan 1200 "Patient X should use the treatment apparatus for 10 minutes a day for a week to perform short sprint exercises to treat symptoms associated with Parkinson's disease." The healthcare professional may select the new treatment plan 1200, and the server 30 may receive the selection. The server 30 may control the treatment apparatus 70 based on the updated treatment plan 1200. In some embodiments, the updated treatment plan 1200 may be transmitted to the patient interface 50 such that the patient may view the details of the new treatment plan 1200. In some embodiments, the updated treatment plan 1200 may be selected and implemented automatically without user input. In some embodiments, the updated treatment plan 1200 may cause a processing device to control the treatment apparatus 70 in real-time or near real-time.

Figure 13:
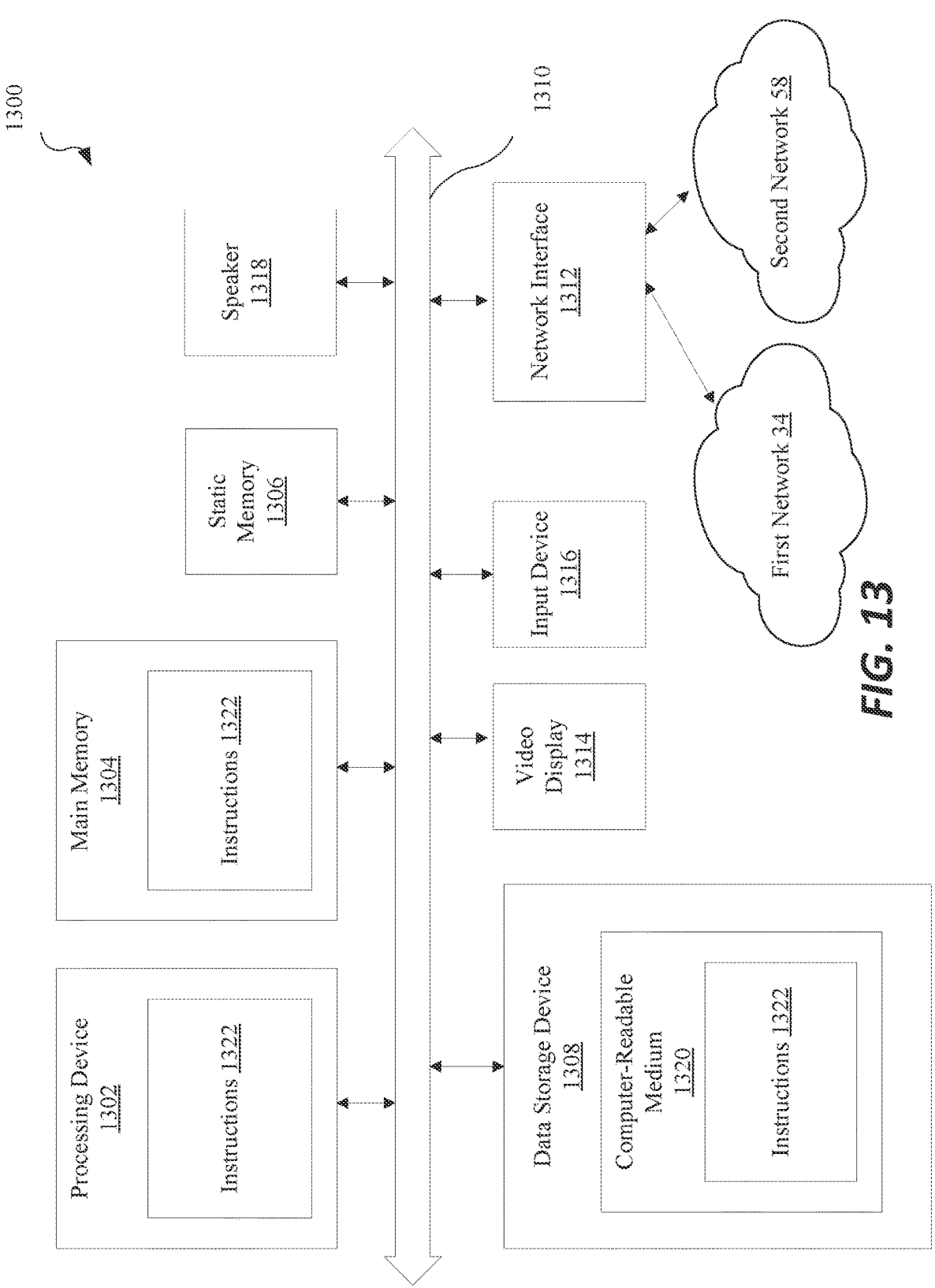
FIG. 13 generally illustrates a computer system according to the principles of the present disclosure.

FIG. 13 shows an example computer system 1300, which can perform any one or more of the methods described herein, in accordance with one or more aspects of the present disclosure. In one example, computer system 1300 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1300 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1300 includes a processing device 1302, a main memory 1304 (e.g., read-only memory (ROM), flash memory, solid state drives (SSDs), dynamic random access memory (DRAM) such as synchronous DRAM (SDRAM)), a static memory 1306 (e.g., flash memory, solid state drives (SSDs), static random access memory (SRAM)), and a data storage device 1308, which communicate with each other via a bus 1310.

Processing device 1302 represents one or more general-purpose processing devices such as a microprocessor, central processing unit, or the like. More particularly, the processing device 1302 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1302 may also be one or more special-purpose processing devices such as an application specific integrated circuit (ASIC), a system on a chip, a field programmable gate array (FPGA), a digital signal processor (DSP), network processor, or the like. The processing device 102 is configured to execute instructions for performing any of the operations and steps discussed herein.

The computer system 1300 may further include a network interface device 1312. The computer system 1300 also may include a video display 1314 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1316 (e.g., a keyboard and/or a mouse or a gaming-like control), and one or more speakers 1318 (e.g., a speaker). In one illustrative example, the video display 1314 and the input device(s) 1316 may be combined into a single component or device (e.g., an LCD touch screen).

The data storage device 1316 may include a computer-readable medium 1320 on which the instructions 1322 embodying any one or more of the methods, operations, or functions described herein is stored. The instructions 1322 may also reside, completely or at least partially, within the main memory 1304 and/or within the processing device 1302 during execution thereof by the computer system 1300. As such, the main memory 1304 and the processing device 1302 also constitute computer-readable media. The instructions 122 may further be transmitted or received over a network via the network interface device 1312.

While the computer-readable storage medium 1320 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A method for updating a treatment plan, wherein the treatment plan is associated with a user using a treatment apparatus to perform the treatment plan, the method comprising: receiving first data associated with a first diagnosis of the user; generating, based on the first data, an initial treatment plan to be performed on the treatment apparatus by the user; receiving second data associated with a first attribute of the user; and generating, via an artificial intelligence engine, a machine learning model trained to generate an updated treatment plan based on the initial treatment plan and the second data.

Clause 2. The method of clause 1, wherein the first attribute is a second diagnosis of the user.

Clause 3. The method of clause 2, wherein at least one of the first and the second diagnoses is a medical diagnosis made by a healthcare professional.

Clause 4. The method of clause 3, wherein the medical diagnosis includes at least a neurological condition.

Clause 5. The method of clause 4, wherein the neurological condition affects a function of the user, wherein the function includes at least one of a somatic function, a psychological function, a behavioral function, a dexterous function, a cerebral function, and a cognitive function.

Clause 6. The method of clause 1, wherein the first attribute is sensor data received from one or more sensors associated with the user.

Clause 7. The method of clause 6, wherein the sensor data comprises at least one of a measurement of a vital sign of the user, a respiration rate of the user, a heartrate of the user, a heart rhythm of a user, an oxygen saturation of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the treatment apparatus, an amount of force exerted on a portion of the treatment apparatus, a range of motion achieved on the treatment apparatus, a speed measurement of a moving portion of the treatment apparatus, a pressure exerted on a portion of the exercise apparatus, an acceleration measurement of a moving portion of the exercise apparatus, a jerk of a portion of the exercise apparatus, a torque level of a portion of the exercise apparatus, and an indication of a plurality of pain levels experienced by the user when using the treatment apparatus.

Clause 8. The method of clause 6, wherein the second data is received in real-time or near real-time.

Clause 9. The method of clause 5, further comprising determining, based on the second data, a first condition of the user.

Clause 10. The method of clause 9, wherein determining the first condition of the user further comprises: transmitting the second data to a computing device associated with a healthcare professional; receiving, by the computing device, the second data; and diagnosing, by the healthcare professional and based on the second data, a medical condition of the user, wherein the medical condition is the first condition.

Clause 11. The method of clause 9, wherein determining a first condition of the user further comprises: transmitting the second data to the artificial intelligence engine; receiving, by the artificial intelligence engine, the second data; and diagnosing, by the artificial intelligence engine, a medical condition of the user, wherein the medical condition is the first condition.

Clause 12. The method of clause 9, wherein the first condition is a neurological condition.

Clause 13. The method of clause 12, wherein the neurological condition affects a function of the user, wherein the function includes at least one of a somatic function, a psychological function, a behavioral function, a dexterous function, a cerebral function, and a cognitive function.

Clause 14. The method of clause 5, wherein the second data is associated with an amount of time the user takes to respond to a stimulus.

Clause 15. The method of claim 14, wherein the stimulus comprises at least one of an audio, visual, and haptic stimuli provided to the user, wherein the audio stimulus includes an audio characteristic associated with at least one of a volume, a cadence, a tone, an enunciation, a word, a language, a dialect, a vernacular, an accent, an emphasis, a pitch, a rhythm, an order of words, a tense, a timbre, and a prosody, wherein the visual stimulus includes a visual characteristic associated with at least one of a color, an image, a video, a text, a font type, a font style, a point size, a font modifier, a virtual-reality environment, and an illumination, and wherein the haptic stimulus includes a haptic characteristic associated with at least one of a vibration, a force, a pressure, a torque, an intensity, a resistance, an electric stimulus, an ultrasonic frequency, a heat level, and a temperature.

Clause 16. The method of clause 15, further comprising determining, based on the second data, a first condition of the user.

Clause 17. The method of clause 16, wherein determining a first condition of the user further comprises: transmitting the second data to an artificial intelligence engine; receiving, by the artificial intelligence engine, the second data; and diagnosing, by the artificial intelligence engine, a medical condition of the user, wherein the medical condition is the first condition.

Clause 18. The method of clause 15, further comprising controlling, based on the updated treatment plan, the treatment apparatus.

Clause 19. A system for updating a treatment plan associated with a user using a treatment apparatus to perform the treatment plan, the system comprising: a processing device; and a memory including instructions that, when executed by the processing device, cause the processing device to: receive first data associated with a first diagnosis of the user; generate, based on the first data, an initial treatment plan to be performed on the treatment apparatus by the user; receive second data associated with a first attribute of the user; and generate, via an artificial intelligence engine, a machine learning model trained to generate an updated treatment plan for the user based on the initial treatment plan and the second data.

Clause 20. The system of clause 19, wherein the memory causes the processing device to determine, based on the second data, a first condition of the user.

Clause 21. The system of clause 20, wherein the memory causes the processing device to determine a first condition of the user by: transmitting the second data to the artificial intelligence engine; receiving, by the artificial intelligence engine, the second data; and diagnosing, by the artificial intelligence engine, a medical condition of the user, wherein the medical condition is the first condition.

Clause 22. The method of clause 21, wherein the first condition includes at least a neurological condition.

Clause 23. The method of clause 22, wherein the neurological condition affects a function of the user, wherein the function includes at least one of a somatic function, a psychological function, a behavioral function, a dexterous function, a cerebral function, and a cognitive function.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A method for updating a treatment plan, wherein the treatment plan is associated with a user using a treatment apparatus to perform the treatment plan, the method comprising, using one or more processors:

receiving first data identifying a first diagnosis of the user, wherein the first diagnosis indicates at least one of a neurological, physiological, or anatomical condition of the user;

generating, based on the first data, an initial treatment plan to be performed on the treatment apparatus by the user;

receiving, from at least one sensor associated with the user or the treatment apparatus, second data indicating a first attribute of the user, wherein the first attribute indicates an amount of time the user takes to respond to a stimulus and the second data includes sensor data obtained by the at least one sensor;

generating an updated treatment plan based on the initial treatment plan and the second data; and controlling, via an artificial intelligence engine, the treatment apparatus based on the updated treatment plan by modifying one or more operating parameters associated with one or more pedals of the treatment apparatus.

2. The method of claim 1, further comprising generating, based on the second data, a second diagnosis of the user.

3. The method of claim 2, wherein at least one of the first and the second diagnoses is a medical diagnosis made by a healthcare professional.

4. The method of claim 3, wherein the medical diagnosis includes at least a neurological condition.

5. The method of claim 4, wherein the neurological condition affects a function of the user, wherein the function includes at least one of a somatic function, a psychological function, a behavioral function, a dexterous function, a cerebral function, and a cognitive function.

6. The method of claim 1, wherein the sensor data comprises at least one of a measurement of a vital sign of the user, a respiration rate of the user, a heartrate of the user, a heart rhythm of a user, an oxygen saturation of the user, a sugar level of the user, a composition of blood of the user, cerebral activity of the user, cognitive activity of the user, a lung capacity of the user, a temperature of the user, a blood pressure of the user, an eye movement of the user, a degree of dilation of an eye of the user, a reaction time, a sound produced by the user, a perspiration rate of the user, an elapsed time of using the treatment apparatus, an amount of force exerted on a portion of the treatment apparatus, a range of motion achieved on the treatment apparatus, a speed measurement of a moving portion of the treatment apparatus, a pressure exerted on a portion of the treatment apparatus, an acceleration measurement of a moving portion of the exercise apparatus, a jerk of a portion of the exercise apparatus, a torque level of a portion of the exercise apparatus, and an indication of a plurality of pain levels experienced by the user when using the treatment apparatus.

7. The method of claim 1, wherein the second data is received in real-time or near real-time.

8. The method of claim 5, further comprising determining, based on the second data, a first condition of the user.

9. The method of claim 8, wherein determining the first condition of the user further comprises:

transmitting the second data to a computing device associated with a healthcare professional;

receiving, by the computing device, the second data; and diagnosing, by the healthcare professional and based on the second data, a medical condition of the user, wherein the medical condition is the first condition.

10. The method of claim 8, wherein determining a first condition of the user further comprises:

transmitting the second data to the artificial intelligence engine;

receiving, by the artificial intelligence engine, the second data; and diagnosing, by the artificial intelligence engine, a medical condition of the user, wherein the medical condition is the first condition.

11. The method of claim 8, wherein the first condition is a neurological condition.

12. The method of claim 11, wherein the neurological condition affects a function of the user, wherein the function includes at least one of a somatic function, a psychological function, a behavioral function, a dexterous function, a cerebral function, and a cognitive function.

13. The method of claim 1, wherein the stimulus comprises at least one of an audio, visual, and haptic stimulus provided to the user, wherein:

the audio stimulus includes an audio characteristic associated with at least one of a volume, a cadence, a tone, an enunciation, a word, a language, a dialect, a vernacular, an accent, an emphasis, a pitch, a rhythm, an order of words, a tense, a timbre, and a prosody, the visual stimulus includes a visual characteristic associated with at least one of a color, an image, a video, a text, a font type, a font style, a point size, a font modifier, a virtual-reality environment, and an illumination, and the haptic stimulus includes a haptic characteristic associated with at least one of a vibration, a force, a pressure, a torque, an intensity, a resistance, an electric stimulus, an ultrasonic frequency, a heat level, and a temperature.

14. The method of claim 13, further comprising determining, based on the second data, a first condition of the user.

15. The method of claim 14, wherein determining a first condition of the user further comprises:

transmitting the second data to the artificial intelligence engine;

receiving, by the artificial intelligence engine, the second data; and diagnosing, by the artificial intelligence engine, a medical condition of the user, wherein the medical condition is the first condition.

16. A system for updating a treatment plan associated with a user using a treatment apparatus to perform the treatment plan, the system comprising:

a processing device; and a memory including instructions that, when executed by the processing device, cause the processing device to:

receive first data identifying a first diagnosis of the user, wherein the first diagnosis indicates at least one of a neurological, physiological, or anatomical condition of the user;

generate, based on the first data, an initial treatment plan to be performed on the treatment apparatus by the user;

receive, from at least one sensor associated with the user or the treatment apparatus, second data indicating a first attribute of the user, wherein the first attribute indicates an amount of time the user takes to respond to a stimulus and the second data includes sensor data obtained by the at least one sensor; and generate an updated treatment plan for the user based on the initial treatment plan and the second data; and control, via an artificial intelligence engine, the treatment apparatus based on the updated treatment plan by modifying one or more operating parameters associated with one or more pedals of the treatment apparatus.

* * * * *